United States Patent
Georgieva et al.

(10) Patent No.: US 9,493,737 B2
(45) Date of Patent: Nov. 15, 2016

(54) METHOD FOR PURIFYING BACTERIAL CELLS

(75) Inventors: Tania Ivanova Georgieva, Soeborg (DK); Anders Clausen, Virum (DK); Tina Malling Thorsen, Naestved (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 14/239,491

(22) PCT Filed: Aug. 20, 2012

(86) PCT No.: PCT/EP2012/066208
§ 371 (c)(1),
(2), (4) Date: Feb. 18, 2014

(87) PCT Pub. No.: WO2013/024178
PCT Pub. Date: Feb. 21, 2013

(65) Prior Publication Data
US 2014/0206067 A1 Jul. 24, 2014

(30) Foreign Application Priority Data

Aug. 18, 2011 (DK) .................. 2011 00625
Feb. 7, 2012 (DK) .................. 2012 00101

(51) Int. Cl.
| | |
|---|---|
| C12N 1/00 | (2006.01) |
| C12N 1/20 | (2006.01) |
| C12N 1/04 | (2006.01) |
| C12R 1/01 | (2006.01) |
| C12R 1/225 | (2006.01) |
| C12R 1/23 | (2006.01) |
| C12R 1/46 | (2006.01) |

(52) U.S. Cl.
CPC . *C12N 1/20* (2013.01); *C12N 1/04* (2013.01); *C12R 1/01* (2013.01); *C12R 1/225* (2013.01); *C12R 1/23* (2013.01); *C12R 1/46* (2013.01)

(58) Field of Classification Search
None
See application file for complete search history.

(56) References Cited

U.S. PATENT DOCUMENTS

| 4,217,419 A | 8/1980 | Suzuki |
|---|---|---|
| 7,037,708 B1 | 5/2006 | Runge et al. |

FOREIGN PATENT DOCUMENTS

| CN | 101649293 | 2/2010 |
|---|---|---|
| CN | 101914475 | 12/2010 |
| EP | 1 680 501 B1 * | 5/2005 |
| WO | WO-99/57242 | 11/1999 |
| WO | WO-2005/060937 | 7/2005 |
| WO | WO-2006/125446 A2 | 11/2006 |
| WO | WO-2010/023248 | 3/2010 |

(Continued)

OTHER PUBLICATIONS

Kurtmann et al., Cryobiology, 2009, vol. 58, p. 175-180.*

(Continued)

*Primary Examiner* — Kade Ariani
(74) *Attorney, Agent, or Firm* — Foley & Lardner LLP

(57) ABSTRACT

The present invention relates to a process for providing purified bacteria-containing concentrates, comprising at least the steps of adding an aqueous solution to a first bacteria-containing concentrate to provide a bacteria-containing suspension, wherein the volume of the added aqueous solution is in the range of 0.3 liters to 10 liters per liter of said first bacteria-containing concentrate; and concentrating said bacteria-containing suspension to provide a second bacteria-containing concentrate. Further, the present invention relates to the purified concentrates per se.

21 Claims, 10 Drawing Sheets

(56) References Cited

FOREIGN PATENT DOCUMENTS

Figure 1:
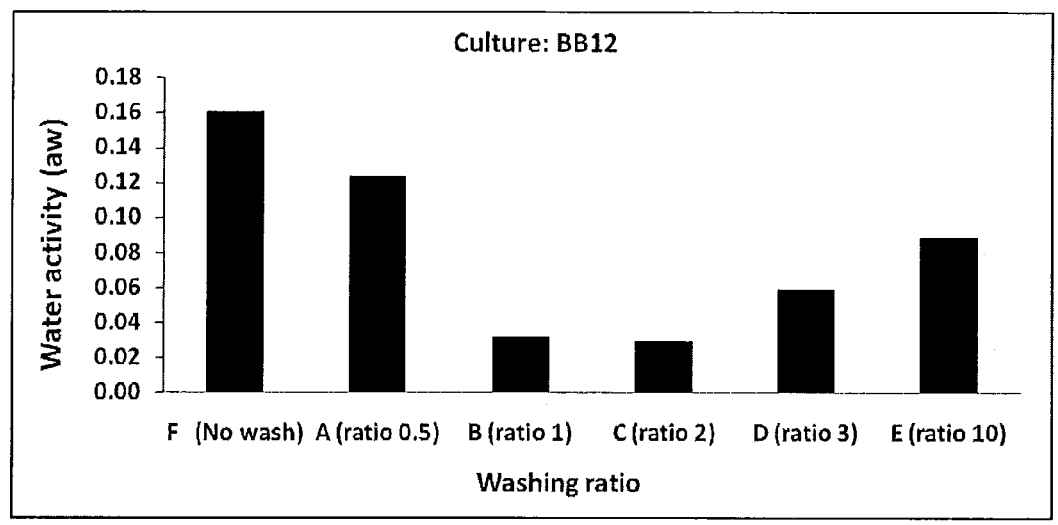

| WO | WO-2011/000883 A2 | 1/2011 |
| WO | WO-2012/076665 | 6/2012 |
| WO | WO-2012/088261 | 6/2012 |

OTHER PUBLICATIONS

Persson et al., Biotechnol Bioeng., 2001, vol. 72, p. 269-277.*
Erdogdu, F. Optimization in Food Engineering, CRC Press, Dec. 9, 2008—Technology & Engineering, pp. 419 and 421 Only.*
Ferreira, V. et al. "Survival of *Lactobacillus sakei* during heating, drying and storage in the dried state when growth has occurred in the presence of sucrose or monosodium glutamate." Biotechnology Letters 27(4) (2005): 249-52.
Fonseca et al., "Collapse temperature of bacterial suspensions: the effect of cell type and concentration," Cryoletters, vol. 25, No. 6, 2004, pp. 425-434.
International Preliminary Report on Patentability mailed Jan. 8, 2014 issued in connection with International Application No. PCT/EP2012/066208.
International Search Report mailed Jan. 30, 2013 issued in connection with International Application No. PCT/EP2012/066208.
Kurtmann, L. et al., "Water activity-temperature state diagrams of freeze-dried *Lactobacillus acidophilus* (La-5): Influence of physical state on bacterial survival during storage." Biotechnol.Prog 25 (2009): 265-70.
Laroche, C. et al., "Water activity affects heat resistance of microorganisms in food powders." International Journal of Food Microbiology, 97.3 (2005): 307-15.
Palmfeldt, J. et al., "Influence of culture pH on survival of *Lactobacillus reuteri* subjected to freeze-drying," Int J Food Microbiol., vol. 55, No. 1-3, 2000, pp. 235-38.
Patel, S. et al., "Determination of End Point of Primary Drying in Freeze-Drying Process Control," AAPS Pharmscitech, vol. 11, No. 1, 2010, pp. 73-84.
Stadhouders et al, "Preservation of starters and mass production of starter bacteria", Neth. Milk Dairy J. 23, 182-199. 1969.
Written Opinion of the International Preliminary Examining Authority mailed Aug. 16, 2013 issued in connection with International Application No. PCT/EP2012/066208.
Zhao G et al: "Influence of freeze-drying conditions on survival of *Oenococcus oeni* for malolactic fermentation", International Journal of Food Microbiology, Elsevier Science Publishers, Amsterdam, NL, vol. 135, No. 1, Sep. 30, 2009, pp. 64-67.
Database WPI Week 201021 Thomson Scientific, London, GB; AN 2010-C44233 XP002688039, & CN 101 649 293 A (Univ China Agric) Feb. 17, 2010.
Database WPI Week 201139 Thomson Scientific, London, GB; AN 20111-A42432 XP002688040, & CN 101 914 475 A (Shandong Baolai Leelai Bioengineering Co) Dec. 15, 2010.
de Valdez et al. "Effect of Drying Medium on Residual Moisture Content and Viability of Freeze-Dried Lactic Acid Bacteria." Appl Environ Microbiol. 49(2) (1985): 413-15.

* cited by examiner

METHOD FOR PURIFYING BACTERIAL CELLS

CROSS REFERENCE TO RELATED APPLICATIONS

The present application is the U.S. national stage of International Application No. PCT/EP2012/066208, filed Aug. 20, 2012, which claims priority from Danish Application No. PA 2011 00625, filed Aug. 18, 2011, and PA 2012 00101, filed Feb. 7, 2012. The entire disclosures of each of the-above-referenced applications are incorporated herein by reference.

FIELD OF THE INVENTION

The present invention relates to a process for providing purified bacteria-containing concentrates, comprising at least the steps of adding an aqueous solution to a first bacteria-containing concentrate to provide a bacteria-containing suspension, wherein the volume of the added aqueous solution is in the range of 0.3 liters to 10 liters per liter of said first bacteria-containing concentrate; and concentrating said bacteria-containing suspension to provide a second bacteria-containing concentrate. Further, the present invention relates to the purified concentrates per se. In an embodiment, the process comprises a washing step followed by a centrifugation step. The process of the invention is particularly suitable for purifying and concentrating bacteria-containing concentrates (e.g., lactic acid bacteria concentrates) obtained from a fermentation broth.

BACKGROUND OF THE INVENTION

Before inoculation into products, such as food products, bacteria are cultured in order to provide a suspension containing large amounts of bacteria. The suspension is usually concentrated using centrifugation, filtration, distillation, sedimentation or flocculation. This concentration step is often followed by freezing or freeze-drying or drying or storage of the microbial concentrate as a frozen product in liquid nitrogen to preserve and/or store the bacteria.

In addition to providing a concentrate of desired bacteria, the concentration step also reduces the volume of the suspension to be treated for preservation and/or storage. By reducing the volume of the suspension and increasing the concentration of the bacteria in the suspension, cost reduction advantages are obtained in downstream processing steps (for example cost reduction of freezing, freeze-drying, drying and transportation). In an industrial scale, the concentrate must remain sufficiently flowable to permit further processing.

However, preservation (such as freezing or freeze-drying) of the bacteria is a bottleneck in the industrial production of storable viable bacteria due to the cell damage and loss of viable cells during the freeze-drying but also due to the long process time and the high costs that are associated with industrial freeze drying processes. Moreover, the amount of water remaining after drying affects not only viability of lactic acid bacteria, as determined immediately after the process, but also the rate of loss of viability during subsequent storage (de Valdez et al. (1985), Appl Environ Microbiol. 49(2):413-15). The initial water activity (aw) of freeze-dried products is very important for the cell survival as higher water activity in the freeze-dried products affects the viability of the bacteria during storage; thus the bacteria are more sensitive to the environmental stresses during storage (Ferreira et al. (2005), Biotechnol Lett, 27(4):249-52). Also, the water activity (aw) is an important factor affecting the stability of dried products and it is used as a critical control point for Hazard Analysis and Critical Control Points (HACCP) programs.

Therefore, there is still a need to improve the efficiency of purification and concentration methods suitable for bacteria-containing suspensions, to obtain a highly concentrated bacteria suspension, more efficient freeze-drying process and a limited loss of activity (i.e., a limited loss of viable bacteria). These methods need to be feasible at any scale, but especially on the industrial scale, where large volumes of suspension are concentrated.

SUMMARY OF THE INVENTION

The present inventors have provided novel processes for purification and concentration of bacteria, and well as processes for preservation of the resulting cells.

It has surprisingly turned out that the purification and concentration method as described herein below has a huge impact on the viability of the bacteria after preservation, such as after a freezing or freeze-drying step. Especially, it has surprisingly been discovered that the bacteria obtained by the process of the invention can be dried faster than cells obtained otherwise, and that the water activity (aw) of the bacteria is significantly lower than expected.

In a first aspect, the present invention in its broadest embodiment relates to a process for purifying ("washing") a bacteria-containing concentrate with an aqueous solution (preferably by using 0.3 liters to 10 liters aqueous solution per liter of the bacteria-containing concentrate) followed by a concentrating step such as centrifugation or filtration.

A presently preferred embodiment of this first aspect relates to a process, preferably a process for improving the storage stability of a bacterial concentrate, comprising the following steps:

b) adding an aqueous solution to a first bacteria-containing concentrate to provide a bacteria-containing suspension, wherein the volume of the added aqueous solution is in the range of 0.3 liters to 10 liters per liter of said first bacteria-containing concentrate;
b1) optionally mixing;
c) concentrating said bacteria-containing suspension to provide a second bacteria-containing concentrate; and
c1) optionally repeating steps b), b1) and c);
c2) optionally adding a cryo protectant and/or a stabilizer.

The process can be used for improving the storage stability of a bacteria-containing concentrate, more preferably a freeze-dried bacteria-containing concentrate. The process can also be used for improving the viability of bacteria upon preservation by freezing or freeze-drying.

In another aspect, the present invention relates to a bacteria-containing concentrate obtainable by a process of the present invention. Preferred concentrates according to the invention contain about 10E9 to about 10E12 cfu/mL and/or are frozen or freeze-dried. Interestingly, such a freeze-dried bacteria-containing concentrate has a lower water activity (aw) than a freeze-dried concentrate produced under identical conditions, but with an unwashed concentrate as a starting material.

DETAILED DISCLOSURE

The present invention relates to processes for the preparation of bacteria-containing concentrates, which comprise at least one washing step as defined below. It was surprisingly found that the processes according to the present invention provide bacteria-containing concentrates that have a reduced water activity ($a_w$), a higher purity and/or whiter colour, and are easier to grind than unwashed concentrates produced under otherwise identical conditions. Further, the resulting bacteria-containing concentrates may be freeze-dried at a higher vacuum than possible for an unwashed concentrate.

In a first aspect, the present invention relates to a process comprising the following steps:
b) adding an aqueous solution to a first bacteria-containing concentrate to provide a bacteria-containing suspension, wherein the volume of the added aqueous solution is in the range of 0.3 liters to 10 liters per liter of said first bacteria-containing concentrate;
b1) optionally mixing;
c) concentrating said bacteria-containing suspension to provide a second bacteria-containing concentrate; and
c1) optionally repeating steps b), b1) and c);
c2) optionally adding a cryoprotectant and/or a stabilizer; and to a process comprising the following steps:
a) providing a first bacteria-containing concentrate;
b) adding an aqueous solution to said first bacteria-containing concentrate to provide a bacteria-containing suspension, wherein the volume of the added aqueous solution is in the range of 0.3 liters to 10 liters per liter of said first bacteria-containing concentrate;
c) concentrating said bacteria-containing suspension to provide a second bacteria-containing concentrate.

In a preferred embodiment the invention thus relates to a process for improving the storage stability of a bacterial concentrate, comprising the following steps:
  a) providing a first lactic acid bacteria-containing concentrate;
  b) adding an aqueous solution to said first lactic acid bacteria-containing concentrate to provide a lactic acid bacteria-containing suspension, wherein the volume of the added aqueous solution is in the range of 0.3 liters to 10 liters per liter of said first lactic acid bacteria-containing concentrate;
  b1) mixing;
  c) concentrating said lactic acid bacteria-containing suspension to provide a second lactic acid bacteria-containing concentrate;
  c1) repeating steps b), b1) and c) at least one time;
  c2) adding at least one cryo protectant and/or a stabilizer; and
  d) freezing or freeze-drying said second lactic acid bacteria-containing concentrate.

The processes according to the present invention provide preferably bacteria-containing concentrates wherein the cell survival, i.e. the percentage of active, i.e. viable, cells relative to the total cell number, is particularly high. It is e.g. preferred that at least 40%, at least 50%, at least 60%, at least 70%, at least 80%, at least 90%, or about 100% of the bacterial cells in the second bacterial concentrate are viable. The skilled person is aware of suitable methods to determine the amount of cells in a concentrate that are viable. For example, flow cytometric methods may be used to quantify active and inactive, i.e. viable and non-viable, cells on the level of energy metabolism. Active cells are detected by a cellular fluorescence staining, which differentiates cells generating a membrane potential from cells without such functional energy metabolism.

In an embodiment of the processes of the invention, the volume of the aqueous solution in step b) is in the range of 0.5 liter to 6 liters per liter of said first bacteria-containing concentrate, such as in the range of 1 liter to 4 liters, in the range of 1.5 liters to 3.5 liters, in the range of 1.0 liters to 3.0 liters, in the range of 1.0 liters to 2.0 liters, in the range of 1.0 liters to 1.5 liters, in the range of 1.5 liters to 2.0 liters, or in the range of 2 liters to 3 liters. It is particularly preferred that the volume of the aqueous solution in step b) is in the range of 0.5 liters to 2.0 liters per liter of said first bacteria-containing concentrate. It is further preferred that the volume of the aqueous solution in step b) is in the range of 1.0 liters to 2.0 liters per liter of said first bacteria-containing concentrate. Further, the volume of the aqueous solution in step b) is preferably more than 0.1 and equal to or below 2 liters per liter of said first bacteria-containing concentrate In a further embodiment, the processes may further comprise a step (d), which is selected from one or more of the following:
i) recovering said second bacteria-containing concentrate; and/or
ii) freezing said second bacteria-containing concentrate; and/or
iii) drying said second bacteria-containing concentrate, such as by freeze-drying, spray-drying, vacuum-drying, microwave-drying, air-drying, fluidized bed drying, drum drying or any combination thereof.

It is presently preferred that the concentrating in step c) is carried out as a centrifugation step, said centrifugation step is preferably carried out at a centrifugation force from about 400 to about 65000×g, preferably from about 4000 to about 20000×g, preferably from about 8000 to about 15000×g. The skilled person will be able to choose the centrifugal force such that only a minor portion of the bacteria in the pellet or concentrate will be rendered non-viable by the centrifugation step(s). For example, after a centrifuging step according to the invention preferably more than 50%, more than 60%, more than 70%, more than 80% or more than 90% of the bacteria that were viable before the centrifugation step was carried out remain viable.

The concentrating in step c) may also be carried out as a filtering step, said filtering step comprises microfiltration, preferably using a filtration membrane having a pore size of 0.1 to 10 micrometers. Alternatively, said filtering step comprises ultrafiltration, preferably using a filtration membrane having a molecular weight cut-off of about 5 to about 200 kDa. The filtering step may comprise tangential filtration, i.e. filtration wherein the concentrate tangentially flows across the surface of the filtration membrane while the permeate flows trough the filtration membrane.

The first bacteria-containing concentrate to be used in step a) and/or b) has preferably been obtained by concentration of a fermentation broth or a culture containing the bacteria. In one embodiment of the processes of the invention, the first bacteria-containing concentrate may be obtained by centrifuging a fermentation broth, e.g. using a continuous centrifuge. The first bacteria-containing concentrate may be in form of a frozen concentrate, a liquid (ambient) concentrate, a pressed concentrate (such as a filter cake), a dried concentrate, a spray dried concentrate, a vacuum dried concentrate or in form of a freeze-dried concentrate.

The first bacteria-containing concentrate is concentrated at a ratio in the range 5 to 25 times, such as 10-20 times, based on the volume of the fermentation broth. Thus, preferably, the first bacteria-containing concentrate has been concentrated 5- to 25-fold, preferably 10- to 20-fold, more preferably about 15-fold, based on the volume of the fermentation broth In an alternative embodiment, the first bacteria-containing concentrate may be obtained by filtration of a fermentation broth, e.g. using tangential filtration and/or ultrafiltration.

In a preferred embodiment, the first bacteria-containing concentrate is obtained by centrifuging a fermentation broth, and the concentrating of the bacteria-containing suspension in step c) is performed by centrifugation. At least one of said centrifuging steps may be carried out at a centrifugation force from about 400 to about 65000×g, preferably from about 4000 to about 20000×g, preferably from about 8000 to about 15000×g.

It should be understood that a convenient implementation of the process of the invention is a continuous flow process.

In a further embodiment, the processes of the invention may further comprise the step of recovering the supernatant obtained in the centrifuging step and/or the permeate obtained in the filtering step.

The pH of the aqueous solutions of step b) may be in the range of 3 to 8, such as in the range 4 to 7 or in the range 3 to 7.

The temperature of the aqueous solution of step b) may be in the range of 0 to 50 degrees C. (° C.), such as in the range 3 to 30 degrees, in the range of 5 to 25 degrees, or in the range of 10 to 20 degrees.

In a further embodiment, one or more, preferably all, of the steps of the processes according to the present invention are carried out at a temperature in the range of 0 to 50 degrees C., such as in the range 3 to 30 degrees C., in the range of 5 to 25 degrees C., or in the range of 10 to 20 degrees C.

In a yet further embodiment, the bacteria-containing concentrate in the processes according to the present invention is a lactic acid bacteria-containing concentrate. Such a bacteria-containing concentrate may comprise a bacteria selected from the group consisting of *Acetobacter, Bifidobacterium, Carnobacterium, Enterococcus, Lactococcus, Lactobacillus, Leuconostoc, Pediococcus, Oenococcus, Propionibacterium*, and *Streptococcus*.

More specifically, the bacteria-containing concentrate may comprise at least one strain of a lactic acid bacteria genus, preferably selected from the group consisting of *Lactococcus, Lactobacillus, Leuconostoc, Carnobacterium, Pediococcus*, and *Streptococcus* and more preferably at least one strain of a species selected from the group consisting of *Leuconostoc* spp., *Bifidobacterium* ssp, *Lactococcus lactis, Lactococcus cremoris, Lactobacillus acidophilus, Lactobacillus casei, Lactobacillus kefir, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sake, Lactobacillus reuteri, Lactobacillus lactis, Lactobacillus delbreuckii, Lactobacillus plantarum*, and *Streptococcus thermophilus*.

In a presently preferred embodiment of the first aspect, the bacteria is of a strain selected from the group consisting of BB-12® that was deposited with the German Collection of Microorganisms and Cell Cultures (DSMZ) under the accession no. DSM15954, BB-12® free that was deposited with the German Collection of Microorganisms and Cell Cultures (DSMZ) under the accession no. DSM17281, LA-5® that was deposited with the German Collection of Microorganisms and Cell Cultures (DSMZ) under the accession no. DSM13241, ST6008 that was deposited with the German Collection of Microorganisms and Cell Cultures (DSMZ) under the accession no. DSM18111, LGG® that was deposited with the American Tissue type Collection Center under the accession no. ATCC53103, ST-4895 that was deposited with the German Collection of Microorganisms and Cell Cultures (DSMZ) under the accession no. DSM19242 and R-607-1 that was deposited with the German Collection of Microorganisms and Cell Cultures (DSMZ) under the accession no. DSM21404, and/or mutants or variants thereof.

In the present context, the term "mutant" should be understood as a strain derived from a mother strain by means of e.g. genetic engineering, radiation, UV light, and/or chemical treatment and/or other methods that induce changes in the genome. It is preferred that the mutant is a functionally equivalent mutant, e.g. a mutant that has substantially the same, or improved, properties as the mother strain. Such a mutant can be used in the processes according to the present invention. Especially, the term "mutant" refers to a strain obtained by subjecting a strain to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood as containing one mutagenization step followed by a screening/selection step), but it is presently preferred that no more than 20, or no more than 10, or no more than 5 treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain.

The number of bacteria in the first bacteria-containing concentrate of step b) may be from about $10^8$ to about $10^{13}$ cfu/mL, such as from $10^8$ to $10^{13}$ cfu/mL, from $10^9$ to $10^{13}$ cfu/mL, from $10^9$ to about $10^{12}$ cfu/mL, or from $10^{10}$ to $10^{12}$ cfu/mL.

The number of bacteria in the second bacteria-containing concentrate of step c) may be from about $10^8$ to about $10^{13}$ cfu/mL, such as from $10^8$ to $10^{13}$ cfu/mL, from $10^9$ to $10^{13}$ cfu/mL, from $10^9$ to about $10^{12}$ cfu/mL, or from $10^{10}$ to $10^{12}$ cfu/mL.

The aqueous solution may be selected from the group consisting of:
  Water, such as demineralized or distilled water;
  An aqueous buffer;
  A solution or suspension comprising 0 to 30% carbohydrate(s), 0 to 30% polysaccharide(s), 0 to 10% inorganic salt(s), 0 to 10% organic salt(s), 0 to 10% protein(s) and/or peptide(s) and/or amino acid(s), 0 to 10% cryoprotectant(s), 0 to 10%, water up to 100%;
  Water containing from 1 to 300 g/l of a carbohydrate, such as sucrose and/or trehalose;
  water containing 1 to 100 g/l of an inorganic salt, such as chloride or phosphate salts of sodium, potassium, calcium, magnesium;
  Water containing amino acids, carboxylic acids, inorganic acids or inorganic bases;
  Water containing carbohydrates wherein suitable carbohydrates include saccharides such as one or more monosaccharides such as dextrose; one or more disaccharides such as sucrose, trehalose or lactose, one or more oligosaccharides, and/or one or more polysaccharides such as dextran, mannan);
  Water containing a buffer selected from the group consisting of a carboxylic acid such as citric acid, an inorganic acid such as phosphate buffer, an inorganic base, and a conjugate base/acid thereto;
  Water containing an alcohol wherein suitable alcohols include a polyhydric alcohol such as a diol and a derivative thereof such as e.g. polyethylene glycol, a triol such as e.g. glycerol, a polyalcohol, and a sugar alcohol such as e.g. sorbitol;

Water containing a protein, a phosphoprotein such as e.g. casein, a peptide, a peptone, yeast extract, malt extract, tryptone, casein peptone, milk, skim milk, a milk buffer, and/or milk powder;

Water containing a surfactant, such as a non-ionic surfactant such as e.g. Tween 80;

Water containing an antioxidant such as an ascorbic acid; and

Water containing a vitamin or a trace element; and any combination of the above solutions.

In some embodiments, a process of the invention may be a continuous flow process comprising: continuously withdrawing the first bacteria-containing concentrate during centrifugation; and continuously withdrawing the second bacteria-containing concentrate during centrifugation. Nevertheless, the process of the invention may also be carried out as a batch process. In some yet additional embodiments, the centrifuging is carried out at a centrifugation force from about 400 to about 65000×g. In some alternative embodiments, the centrifuging is carried out at a centrifugation force from about 4000 to about 20000×g.

As described above, the concentrating in step c) may also be carried out as a filtering step, such as a microfiltration and/or an ultrafiltration step. In some embodiments, a filtering step comprises microfiltration. In some still further embodiments, a filtering step utilizes a filtration membrane having a pore size of about 0.1 to about 10 micrometers, preferably 0.2 to 5 micrometers, more preferably 0.5 to 2 micrometers. Such microfiltration membranes typically have a molecular weight cut-off of about 200 kDa to about 5 000 kDa. In further embodiments, a filtering step comprises ultrafiltration. In some still further embodiments, an ultrafiltration step utilizes a filtration membrane having a molecular weight cut-off of about 5 to about 200 kDa, preferably 10 to 100 kDa, more preferably 40 to 80 kDa. In some alternative embodiments, filtering comprises tangential filtration.

In some processes of the present invention, the filtration step is accomplished using microfiltration with a microfiltration membrane having a pore size from about 0.1 to about 10 micrometers, while in other embodiments the pore size is from about 0.1 to about 5 micrometers, and in still other embodiments, the pore size is from about 0.1 to about 2 micrometers. In some preferred embodiments, the microfiltration membrane has a molecular weight cut-off of about 200 kDa to about 5 000 kDa, while in other embodiments, the molecular weight cut-off is about 250 kDa to about 1 000 kDa, and in still other embodiments, the molecular weight cut-off is about 500 kDa.

In some alternative processes of the present invention, the filtration step is accomplished using ultrafiltration with an ultrafiltration membrane having a pore size from about 0.01 micrometers to about 0.1 micrometers, while in other embodiments, the pore size is from about 0.02 to about 0.1 micrometers, and in still other embodiments, the pore size is from about 0.05 to about 0.1 micrometers. In some embodiments, the ultrafiltration membrane has a molecular weight cut-off of about 5 kDa to about 200 kDa, while in other embodiments, the molecular weight cut-off of is from about 30 kDa to about 200 kDa, and in still further embodiments, the molecular weight cut-off is about 150 kDa.

The process according to the present invention may comprise a step (d) (i) wherein said second bacteria-containing concentrate is recovered. Thus, in some further embodiments, the processes further comprise the step of recovering the supernatant and/or permeate obtained after the centrifuging step and/or the filtering step.

The processes of the present invention provide means for the rapid and efficient concentration of bacteria-containing suspensions. Importantly, the processes of the present invention find use on an industrial scale, as significant volumes of bacteria-containing suspensions can be treated. In some embodiments, the processes of the present invention find use in treating suspensions of about 500 L to about 100,000 L. In some embodiments, the suspensions range from about 10,000 L to about 50,000 L, while in other embodiments, the range is from about 10,000 L to about 25,000 L. However, it is not intended that the present invention be limited to these volumes, as it is contemplated that any suitable volume of bacteria-containing suspension will find use in the processes of the present invention.

Furthermore, the processes of the present invention facilitate economical and efficient additional processing of the bacterial suspensions. For example, because the water content of concentrate is lower and the bacteria concentration is higher than suspensions produced using other processes, freeze-drying and lyophilisation of these suspensions is accomplished faster and more efficiently than by using standard processes. Thus, by providing more rapid, efficient and economical means to preserve and store cultures, the present invention provides for reductions in energy, materials, and transportation costs.

In some embodiments, a process of the present invention involves at least two washing steps. Thus, in these embodiments a step c1) is carried out wherein the steps b), b1) and c) are repeated at least once.

In another embodiment, the process comprises a washing step followed by a centrifugation step.

In some further embodiments, the supernatant obtained after a centrifugation step(s) and/or the permeate obtained after a filtration step(s) are recovered. These embodiments find particular use when molecules of interest are present in the supernatant and/or in the permeate. Some examples of molecules of interest include, but are not limited to bacteriocins, enzymes and lactic acid. In some embodiments, the supernatant obtained after a centrifugation step(s) and/or the permeate obtained after a filtration step(s) are subject to multiple centrifugation and/or filtration step(s) before the recovery of the molecule(s) of interest.

As indicated above, in some embodiments, the processes of the present invention further comprise preservation and/or storage steps. In some embodiments, freeze-drying, drying, freezing and/or cooling find use. Any suitable process finds use in the present invention. For example, drying can be accomplished using drum-drying, spray-drying, fluid bed drying, tray-drying, or any other suitable process. It is not intended that the present invention be limited to any particular preservation and/or storage steps.

The processes of the present invention find use in providing a highly concentrated concentrate of any suitable bacteria, including but not limited to bacteria, viruses, fungi (e.g., molds and, yeasts), protozoans or algae.

In some embodiments, the bacteria-containing suspension is a fermentation broth containing bacteria. In some preferred embodiments, the bacteria comprise one or more of the genera *Bifidobacterium, Lactobacillus, Streptococcus*, and *Lactococcus*. However, it is not intended that the present invention be limited to any particular genus or species of bacteria.

As indicated herein, the process of the present invention are particularly useful and cost effective for providing bacteria-containing concentrates on an industrial scale, where large volumes are treated (e.g., about 500 L to about 100,000 L).

In some embodiments, the centrifugation step(s) considerably reduces the volume of suspension, resulting in a concentrate. The centrifugation step(s) may result in concentration rates of about 5 to about 25.

It is clear to the skilled person that a centrifugation step may be replaced by another concentrating unit operation, e.g. a filtration step, convenient continuous filtration, such as tangential (cross-flow) ultra filtration. Also, the cell wash may be integrated in a concentration step, e.g. if the second bacteria containing concentrate is obtained by means of tangential filtration, it is contemplated that the aqueous solution may be added during the filtration process. In such a case, it is further contemplated that the aqueous solution may be added in 50% of the amount needed when the second bacteria containing concentrate is obtained by means of continuous centrifugation. Thus, the first aspect of the invention also relates to a process comprising the following steps:
b) adding an aqueous solution to a first bacteria-containing concentrate to provide a bacteria-containing suspension, wherein the volume of the added aqueous solution is in the range of 0.15 liters to 5 liters per liter of said first bacteria-containing concentrate;
c) concentrating said bacteria-containing suspension to provide a second bacteria-containing concentrate; and
c1) optionally repeating steps b), and c);
c2) optionally adding a cryo protectant and/or a stabilizer; wherein steps b) and c) are combined in a tangential flow filtration process;
and to a process comprising the following steps:
b) adding an aqueous solution to said first bacteria-containing concentrate to provide a bacteria-containing suspension, wherein the volume of the added aqueous solution is in the range of 0.15 liters to 5 liters per liter of said first bacteria-containing concentrate;
c) concentrating said bacteria-containing suspension to provide a second bacteria-containing concentrate;
wherein steps b) and c) are combined in a tangential flow filtration process. Step b) may be preceded by a step a) which includes providing a first bacteria-containing concentrate;

In such a process, the volume of the aqueous solution may be in the range of 0.25 liter to 3 liters per liter of said first bacteria-containing concentrate, such as in the range of 0.5 liter to 2 liters, in the range 0.75 liters to 1.75 liters, in the range 0.5 liters to 1.5 liters, in the range 0.5 liters to 1.0 liter, in the range 0.5 liters to 0.75 liters, in the range 0.75 liters to 1.0 liter, or in the range 1.0 liter to 1.5 liters.

An interesting embodiment is a process comprising the following steps:
a) concentrating a fermentation broth by centrifugation, providing a first bacteria-containing concentrate, preferably a lactic acid bacteria-containing concentrate;
b) washing said first bacteria-containing concentrate by adding an aqueous solution to said concentrate to provide a bacteria-containing suspension, wherein the volume of the added aqueous solution is in the range of 1.0 liters to 3.0 liters, preferably 0.5 liters to 2.0 liters, per liter of said first bacteria-containing concentrate;
c) concentrating said bacteria-containing suspension by centrifugation to provide a second bacteria-containing concentrate; and
d) drying said second bacteria-containing concentrate, such as by freeze-drying or spray-drying.

Another interesting embodiment is a process comprising the following steps:
a) concentrating a fermentation broth by centrifugation, providing a first bacteria-containing concentrate, preferably a lactic acid bacteria-containing concentrate;
c) washing and concentrating said first bacteria-containing concentrate, to providing a second bacteria-containing concentrate, using tangential ultrafiltration and before and/or during said ultrafiltration adding an aqueous solution to said first bacteria-containing concentrate, wherein the volume of the added aqueous solution is in the range of 0.5 liters to 3.0 liters per liter of said first bacteria-containing concentrate; and;
d) drying said second bacteria-containing concentrate, such as by freeze-drying or spray-drying.

In the two preceding embodiments, it should of course be understood that more washing steps, more centrifugation steps, and/or more filtration steps may be added.

In a second aspect, the present invention relates to a bacteria-containing concentrate obtainable by the processes of the invention. Such a concentrate may have a bacteria concentration from about $10^9$ to about $10^{12}$ cfu/mL. In an advantageous embodiment, the bacteria-containing concentrate obtained by the processes of the invention will be submitted to further processing steps, such as freezing, pressing, drying and/or freeze drying. Thus, the bacteria-containing concentrate may be in form of a frozen concentrate, a liquid (ambient) concentrate, a pressed concentrate (such as a filter cake), a dried concentrate, a spray dried concentrate, a vacuum dried concentrate or in form of a freeze-dried concentrate.

In an embodiment, the bacteria-containing concentrate according to the invention may be in form of a freeze-dried concentrate that has lower water activity ($a_w$) than a freeze-dried concentrate produced under identical conditions, but with an unwashed concentrate.

In another embodiment, the bacteria-containing concentrate of the invention has been freeze-dried at a higher vacuum than possible for an unwashed concentrate, such as at a pressure in a range of 0.2-1.2 mBar, such as in the range of 0.3-0.9 mBar.

It yet another embodiment of the second aspect of the invention, the bacteria-containing concentrate may be in form of a freeze-dried concentrate that has a higher purity and/or whiter colour than the freeze-dried concentrate produced under identical conditions, but with an unwashed concentrate.

In a further embodiment, the bacteria-containing concentrate may be in the form of a freeze-dried concentrate that is easier to grind than the freeze-dried concentrate produced under identical conditions, but with an unwashed concentrate.

In some embodiments, the bacteria-containing concentrate contains a high number of bacteria per volume, at least about $10^9$ to about $10^{12}$ cfu/mL, while in other embodiments, the final concentration is at least about $5.10^9$ to about $9.10^{11}$ cfu/mL.

The concentrate may be dried (e.g. by spray drying, vacuum drying, freeze drying, or by a combination thereof) using conventional techniques, e.g. as disclosed in U.S. Pat. No. 7,037,708B1, WO99057242, and Stadhouders et al. (1969), Neth. Milk Dairy J, 23:182-199.

The concentrates find use in various applications, including, but not limited to food production, feed production, pharmaceutical production (e.g. as active ingredient in health beneficial probiotic products), etc. As indicated above, the present invention finds use in providing concentrates of any suitable bacteria.

As indicated above, a process of the present invention provides means to obtain the desired final concentration of bacteria. The activity level of the bacteria concentrates is directly linked to the number of viable bacteria. In some embodiments, the activity of the bacteria (i.e., the microbial activity level) is determined by assessing the amount of metabolite(s) the culture produces over a given time period and utilizing a specific type of substrate. For example, for lactic acid bacteria, it is possible to determine the activity level by continuously recording the pH for a given period of time, as the pH of a lactic acid bacterial culture is directly linked to the concentration of viable bacteria. In some embodiments, comparing the recorded pH measurement to an expected theoretical pH value based on the assumption that all of the bacteria in the culture are viable, provides the concentration and activity level of the suspension. Thus, if the measured pH is close to the theoretical value, the bacterial population has undergone limited activity loss during the process.

In still another embodiment, the invention relates to a particularly useful freeze-drying process for drying a bacteria-containing concentrate which optionally contains one or more additives, such as a cryo protectant and/or a stabilizer, said process comprising:
i) freezing said bacteria-containing concentrate; and
ii) freeze-drying said frozen bacteria-containing concentrate obtained in step i);
wherein step ii) is performed under the following conditions:
a) a pressure in the range of 0.2 to 2.0 mBar; and
b) a heating plate temperature in the range of 30 to 100 degrees C.

In a preferred embodiment, the optional additive is selected from the group consisting of inosine, inositol, IMP, trehalose, sucrose, maltodextrin and protein hydrolyzate.

Preferably, the pressure that is applied during the freeze-drying step is in the range of 0.5 to 2.0 mBar, more preferably in the range 0.5 to 1.0 mBar, 0.6 to 0.8 mBar, and even more preferably 0.5 to 0.6 mBar. The pressure applied during the freeze-drying step may also be in the range of 0.8 to 1.5 mBar, 0.8 to 1.1 mBar, 0.7 to 1.1 mBar, 0.4 to 0.6 mBar, 0.9 to 1.3 mBar, or 1.0 to 1.9 mBar.

The pressure applied during the freeze-drying step is preferably maintained for a certain time period, e.g. for more than 1 hour, more preferably for more than 2, 3, 4, 5, or even more than 7 hours.

During the freeze-drying, it is particularly preferred to adjust the temperature of the heating unit of the freeze-drying device, e.g. the heating plate, to a temperature in the range of 40 to 90 degrees C., preferably 50 to 85 degrees C., more preferably 55 to 80 degrees C., and even more preferably in the range 60 to 75 degrees C. It has been proven particularly useful to maintain this temperature of the heating unit, e.g. the heating plate, for more than 1 hour, more preferably for more than 2, 3, 4, 5, or more than 7 hours.

The drying process is performed until at least 80%, preferably at least 90% or at least 95%, of the water is removed.

The drying process is preferably performed in a freeze-drying device which is characterized by one or more of the following features:
a) the size of the freeze-dryer is such that it allows to process a batch size of more than 100 kg; and/or
b) the number of shelves and/or heating units, e.g. the heating plates, is more than 10; and/or
c) the thickness of the frozen, bacteria-containing layer on the product tray is 1 to 50 mm at the beginning of the freeze drying process.

In another preferred aspect, the invention relates to an improved freeze-drying process for drying a bacteria-containing concentrate which contains inosine, inositol, trehalose and/or sucrose, said process comprising:
i) freezing said bacteria-containing concentrate; and
ii) freeze-drying said frozen bacteria-containing concentrate obtained in step i);
wherein step ii) is performed under the following conditions:
a) a pressure in the range of 0.3 to 0.6 mBar; and
b) a heating plate temperature in the range of 40 to 80 degrees C.; and wherein the conditions are kept for more than 1 hour, and/or until at least 75% of the water is removed.

The bacteria-containing concentrate used in the improved freeze-drying process comprises at least one lactic acid bacteria genus, preferably selected from the group consisting of *Lactococcus, Lactobacillus, Leuconostoc, Carnobacterium, Pediococcus*, and *Streptococcus* and more preferably at least one species selected from the group consisting of *Leuconostoc* spp., *Bifidobacterium* ssp, *Lactococcus lactis, Lactococcus cremoris, Lactobacillus acidophilus, Lactobacillus casei, Lactobacillus kefir, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sake, Lactobacillus reuteri, Lactobacillus lactis, Lactobacillus delbreuckii, Lactobacillus plantarum*, and *Streptococcus thermophilus*. It is particularly preferred that bacteria in the bacteria-containing concentrate belong to one of the above species.

Preferably, the bacteria-containing concentrate to by dried by use of the improved freeze-drying process is the "second bacteria-containing concentrate" obtained in step c of the process referred to in claim 1-25. This "second bacteria-containing concentrate" optionally contains one or more additives, such as a cryo protectant and/or a stabilizer as defined herein.

Finally, the invention also provides dry bacteria-containing concentrate that is obtainable by the improved freeze-drying process disclosed herein. Preferably, this bacterial concentrate comprises from $10^9$ to $10^{13}$ cfu/g lactic acid bacteria cells.

The improved freeze-drying process of the present invention shall not include any one of the following embodiments:
A) LGG (ATCC 53103) dried under a pressure of 0.2, 0.7, 1.3, 2.0, or 2.5 mBar at a heating unit and/or heating plate and/or shelf temperature of 50 degrees C.,
B) LGG (ATCC 53103) dried under a pressure of 0.2, or 1.3 mBar at a heating unit and/or heating plate and/or shelf temperature of 60 degrees C., and/or
C) LGG (ATCC 53103) dried under a pressure of 0.2 or 1.3 mBar at a heating unit and/or heating plate and/or shelf temperature of 70 degrees C.

These embodiments are disclaimed from the scope of the present invention.

DEFINITIONS

Unless defined otherwise herein, all technical and scientific terms used herein have the same meaning as commonly understood by one of ordinary skill in the art to which this invention pertains. Although any process and materials similar or equivalent to those described herein find use in the practice of the present invention, the preferred process and materials are described herein. Accordingly, the terms defined immediately below are more fully described by reference to the specification as a whole. It is to be understood that the present invention is not limited to the particular methodology, protocols, and reagents described, as these may vary, depending upon the context in which they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. Furthermore, the citation of any document is not to be construed as an admission that it is prior art with respect to the present invention.

A "washing step" as used herein refers a process step in which the bacteria-containing concentrates are admixed with an aqueous solution. Thus, a washing step normally comprises the addition of an aqueous solution to a bacteria-containing concentrate according to the invention. A washing step may additionally comprise removal of a part of the previously added aqueous solution, such as e.g. by centrifugation or filtration. Washing steps in the sense of the present invention may be carried out successively, e.g. by several successive addition and removal steps in a continuous flow process (see below).

As used herein, the term "centrifugation" refers to a method of separating immiscible liquids or solids from liquids through application of centrifugal force. In some preferred embodiments, the separation methods involve subjecting a fluid-containing mixture to a high gravitational force (g). Upon application of this centrifugal force (often many times the force of gravity [×g]), the different components present in the mixture are separated. In some preferred embodiments of the present invention, centrifugation is applied to a liquid containing microbial cells. At the completion of the centrifugation process, the microbial cells are located in the "concentrate" (i.e., the more "solid" portion of the product) and the liquid is the "supernatant" (or "eluate"). In some preferred embodiments, the liquid portion contains no or very few bacteria. In industrial scale volumes, the concentrate typically contains from between about 5 percent and about 20 percent solids.

In some preferred embodiments, centrifugation is carried out in a centrifuge that provides a gravitational force from about 400 to about 65000×g (i.e., times gravity), while in other embodiments, the gravitational force is from about 4000 to 20000×g, and in other embodiments, the gravitational force is from about 6000 to about 10000×g. However, it is not intended that the present invention be limited to any particular centrifuge or gravitational force. In some further embodiments of the present invention the centrifugation step is repeated between about two and about four times. In some particularly preferred embodiments, the centrifugation step is repeated twice. However, it is not intended that the present invention be limited to any particular number of repetitions of the centrifugation step, as any suitable number of repetitions will find use.

As used herein, the term "filtration" refers to a separation process consisting of passing a solution through a filtration membrane to separate the components within the liquid, based on the size of the components. The filtration membrane has pores of a given size designed to retain components that are larger than the pore size, but allow components that are smaller than the pore size to pass through the membrane. Thus, in some preferred embodiments, the solution contains solid elements (e.g., bacteria) that are larger than the pores of the filtration membrane. In these embodiments, the bacteria are present in the "concentrate" (or "retentate") and the liquid phase that passes through the membrane is referred to as "permeate" or "filtrate". In addition to containing liquid, in some embodiments, the permeate also contains other components. In some embodiments of a process of the present invention, the filtration step results in the production of the "second bacteria-containing concentrate". In "conventional filtration" the separation is carried out due to natural gravitational pressure, while in "pressure filtration," additional pressure (e.g., greater pressure on the concentrate side and/or a depression on the permeate side) helps to accelerate the filtration process. Any suitable filtration methods find use in the present invention, including but not limited to microfiltration and ultrafiltration. However, in some particularly preferred embodiments, ultrafiltration is used.

As used herein, the term "micro filtration" refers to any filtration method that involves use of microporous filtration membranes. The pore size of these microfiltration membranes is usually about 0.1 micrometers to about 10 micrometers, preferably 0.2 to 5 micrometers, more preferably 0.5 to 2 micrometers. The microfiltration membranes used in the methods of the present invention typically have a molecular weight cut-off of about 200 kDa to about 5 000 kDa.

As used herein, the term "ultrafiltration" refers to any filtration process using filtration membranes having smaller pore sizes than those used for microfiltration, usually about 0.01 micrometers to about 0.1 micrometers, preferably 0.04 to 0.08 micrometers. The ultrafiltration membranes used in the processes of the present invention typically have a molecular weight cut-off of about 5 kDa to about 200 kDa, preferably 10 to 100 kDa, more preferably, 40 to 80 kDa.

It is intended that any suitable filtration method will find use in the present invention, including but not limited to conventional filtration methods (e.g., by use of gravitational force) and tangential or cross-flow filtration methods. The term "cross flow filtration" and "tangential filtration" are used interchangeably herein in reference to any filtration method wherein the concentrate continuously and tangentially flows across the surface of the filtration membrane while the permeate flows trough the filtration membrane.

In continuous flow processing, the centrifuge is continuously fed with the bacteria-containing suspension providing a continuous output flow of first bacteria-containing concentrate. In the processes of the present invention, a concentration step may be combined with a washing step, e.g. by using diafiltration.

The "water activity" $a_w$ as used herein is defined as the vapor pressure of water in the substance (e.g. the bacteria-containing concentrate of the invention), divided by the vapor pressure of pure water at the same temperature. The skilled person is aware of numerous methods to determine the water activity of a given substance. For example, $a_w$ may be determined by measuring the vapor pressure in the substance and comparison of this vapor pressure with that of water at the same temperature.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria.

Preferably, the lactic acid bacteria are lactic acid bacteria selected from the group consisting of: lactic acid bacteria belonging to genus *Lactobacillus*, such as *Lactobacillus helveticus*, *Lactobacillus delbruekii* subsp. *bulgaricus*, *Lactobacillus fermentum*, *Lactobacillus salivarius* or *Lactobacillus rhamnosus*; lactic acid bacteria belonging to genus *Lactococcus*, such as *Lactococcus lactis*; lactic acid bacteria belonging to genus *Streptococcus*, such as *Streptococcus thermophilus*; lactic acid bacteria belonging to genus *Leuconostoc*, such as *Leuconostoc lactis* or *L. mesenteroides*; lactic acid bacteria belonging to genus *Bifidobacterium*, such as *Bifidobacterium longum*, *Bifidobacterium animalis*, or *Bifidobacterium breve*; lactic acid bacteria belonging to genus *Propionibacterium*; lactic acid bacteria belonging to genus *Enterococcus*, such as *Enterococcus faecum*; and lactic acid bacteria belonging to genus *Pediococcus*.

Even more preferably, the lactic acid bacteria are lactic acid bacteria selected from the group consisting of: *Lactobacillus acidophilus*, *Lactobacillus rhamnosus*, *Bifidobacterium animalis*, *Streptococcus thermophilus* and *Lactococcus lactis*.

Most preferably, the lactic acid bacteria are lactic acid bacteria selected from the group consisting of:
*Lactobacillus acidophilus*, LA-5® that was deposited with the German Collection of Microorganisms and Cell Cultures (DSMZ) under the accession no. DSM13241,
*Bifidobacterium animalis*, BB-12® that was deposited with the German Collection of Microorganisms and Cell Cultures (DSMZ) under the accession no. DSM15954,
*Lactobacillus rhamnosus*, LGG® that was deposited with the American Tissue type Collection Center under the accession no. ATCC53103,
*Streptococcus thermophilus* ST6008 (also referred to as CHCC6008) that was deposited with the German Collection of Microorganisms and Cell Cultures (DSMZ) under the accession no. DSM18111,
*Lactococcus lactis*, R-607-1 (also referred to as CHCC1915) that was deposited with the German Collection of Microorganisms and Cell Cultures (DSMZ) under the accession no. DSM21404.

*Streptococcus thermophilus* strain ST10255 is commercially available from Chr. Hansen A/S as F-DVS ST-BODY-2, Material No: 623155.)

These strains are well known to the person skilled in the art, and are commercially available from Chr. Hansen A/S.

*Streptococcus thermophilus*, ST-4895 was deposited with the German Collection of Microorganisms and Cell Cultures (DSMZ) under the accession no. DSM19242. This deposit was made according to the Budapest treaty on the international recognition of the deposit of microorganisms for the purposes of patent procedure. The Applicant requests that a sample of the deposited microorganism should be made available only to an expert approved by the Applicant.

"Fermentation" means the conversion of carbohydrates into alcohols or acids through the action of bacteria. Preferably, fermentation in the methods of the invention comprises conversion of lactose to lactic acid. Fermentation processes to be used are well known and the person of skill in the art will know how to select suitable process conditions, such as temperature, pH, oxygen, amount and characteristics of bacteria(s) and process time. Obviously, fermentation conditions are selected so as to support the achievement of the present invention, i.e. to produce (or propagate) bacteria.

A "concentrate" as used herein is a bacteria containing culture that has been concentrated, i.e. the relative number of bacteria has been increased by decreasing the overall volume of the culture, e.g. by removing liquid.

Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

Lactic acid bacteria, including bacteria of the species *Lactobacillus* and *Bifidobacterium* are commonly used as probiotic cultures in foods such as fermented milks, yoghurts and cheese, as well as dietary supplements where the probiotic is in the form of a dried product.

A "cryoprotectant" is defined herein is a substance used to protect bacteria cells from damage during freezing, freeze-drying and thawing. The cryoprotectant may be any additive as long as it protects cells from damage during freezing, freeze-drying and thawing. Examples of cryoprotectants include, but are not limited to, sugars (e.g. sucrose, fructose, trehalose), polyalcohols (e.g. glycerol, sorbitol, mannitol), polysaccharides (e.g. celluloses, starch, gums, maltodextrin), polyethers (e.g. polypropylene glycol, polyethylene glycol, polybutylene glycol), antioxidants (e.g. natural antioxidants, such as ascorbic acid, beta-carotene, vitamin E, glutathione, or chemical antioxidants), oils (e.g. rapeseed oil, sunflower oil, olive oil), surfactants (e.g. Tween 20, Tween 80, fatty acids), peptones (e.g. soy peptones, wheat peptone, whey peptone), tryptones, vitamins, minerals (e.g. iron, manganese, zinc), hydrolysates (e.g. protein hydrolysates such as whey powder, malt extract, soy), amino acids, peptides, proteins, nucleic acids, nucleotides, nucleobases (e.g. cytosine, guanine, adenine, thymine, uracil, xanthine, hypoxanthine, inosine, inositol), yeast extracts (e.g. yeast extracts of *Saccharomyces* spp., *Kluyveromyces* spp., or *Torula* spp.), beef extract, growth factors, and lipids. Other examples of cryoprotectants are disclosed in WO2012088261, WO2012076665 which are incorporated herein by reference. The addition of a cryoprotectant in a process of the invention may be done by mixing a solid cryoprotectant with the bacteria concentrate for a sufficient time period at a suitable temperature.

The term "active" (bacterial) cells as used herein refers to the number of viable cells. The amount of active, i.e. viable, cells may be specified in any unit or measure that is commonly used in the art. For example, the amount of active cells may be given in the number of viable cells per gram sample. The "total" number of (bacterial) cells as used herein refers to the sum of active, i.e. viable, and inactive, i.e. non-viable, cells. Preferably, the total number of cells is given in absolute terms, such as the total number of cells per gram sample. The "cell survival" as used herein refers to the percentage of active cells relative to the total number of cells.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

LEGENDS TO FIGURES

FIG. 1. Culture BB-12: Comparison of unwashed and washed concentrates with respect to a potential effect of the washing ratio on the water activity of freeze-dried products. The washing ratio was from 0.5 to 10 volumes water per one volume concentrate. (A) washing ratio 0.5; (B) washing ratio 1; (C) washing ratio 2; (D) washing ratio 3; (E) washing ratio 10; (F) No washing.

Figure 2:
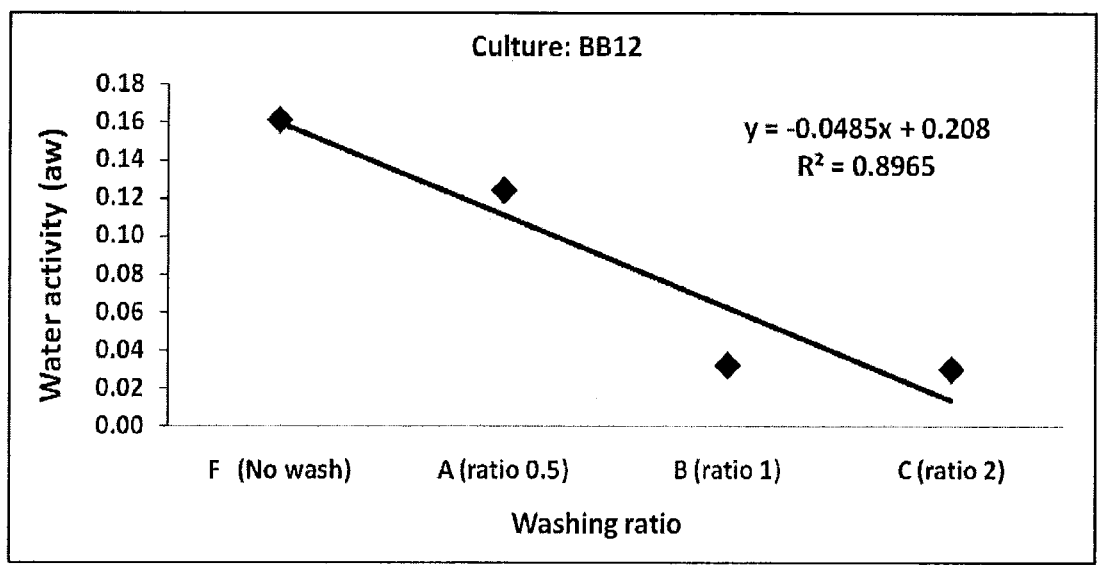

FIG. 2. Culture BB-12: Relationship between the water activity of freeze-dried products and the washing ratio in a range of 0.5-2 volumes water per one volume concentrate. (A) washing ratio 0.5; (B) washing ratio 1; (C) washing ratio 2; (F) No washing. The line represents the linear fit to the data with coefficient of determination $R^2$=0.89. Equation for the linear fit: Y=−0.0485*X+0.208.

Figure 3:
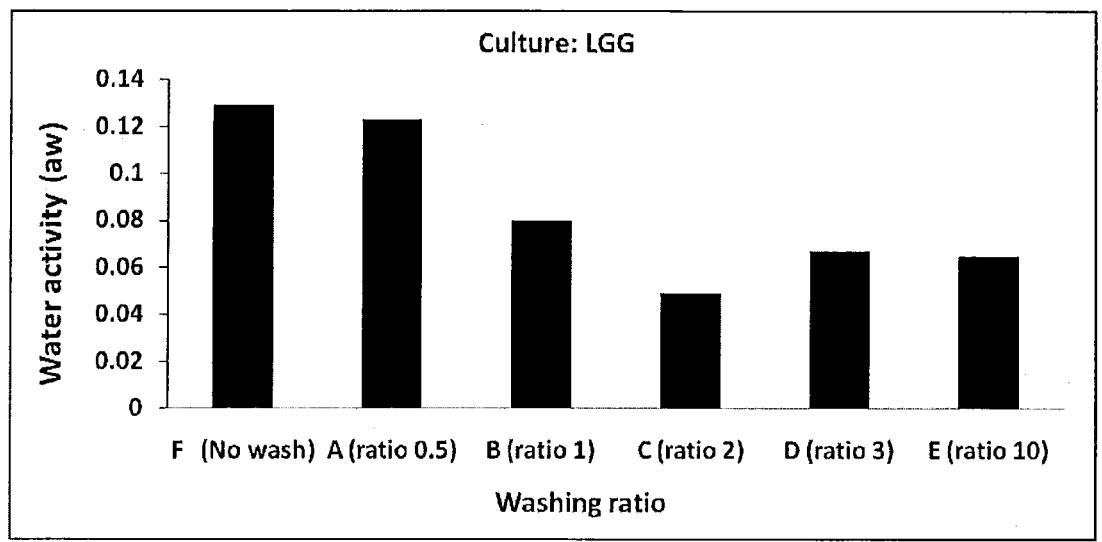

FIG. 3. Culture LGG: Comparison of unwashed vs. washed concentrate with respect to effect of the washing ratio on the water activity of freeze-dried products. The washing ratio was from 0.5 to 10 volumes water per one volume concentrate. (A) washing ratio 0.5; (B) washing ratio 1; (C) washing ratio 2; (D) washing ratio 3; (E) washing ratio 10; (F) No washing.

Figure 4:
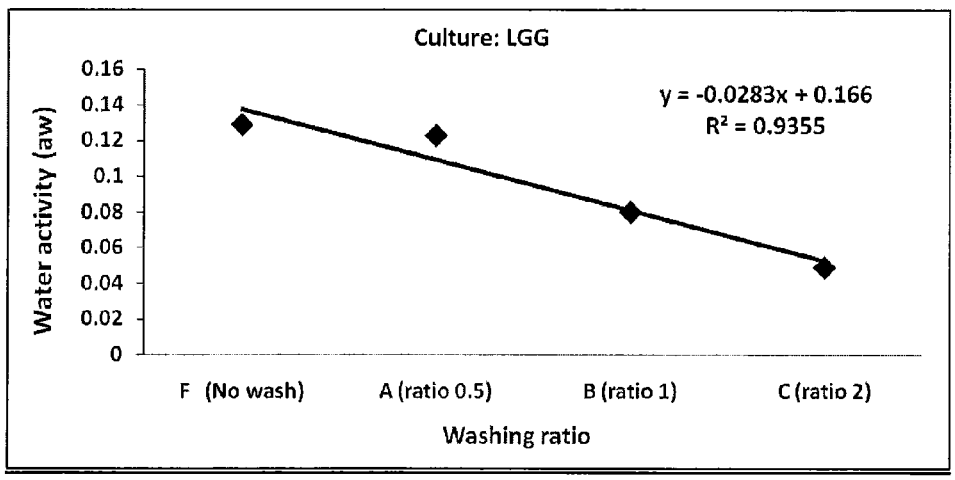

FIG. 4. Culture LGG: Relationship between the water activity of freeze-dried products and the washing ratio in a range of 0.5-2 volumes water per one volume concentrate (A) washing ratio 0.5; (B) washing ratio 1; (C) washing ratio 2; (F) No washing. The line represents the linear fit to the data with coefficient of determination $R^2$=0.93. Equation for the linear fit: Y=−0.0283*X+0.166.

Figure 5:
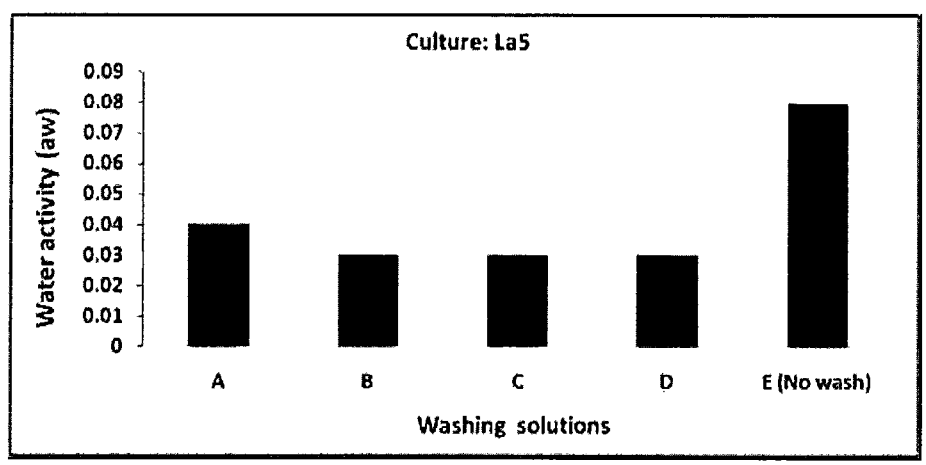

FIG. 5. Culture La-5: Comparison of water activity of freeze-dried products of unwashed and washed cell concentrates with respect to effect of different washing solutions on the water activity. The washing ratio was 2, i.e. 2 volumes washing solution per one volume concentrate. Washing solutions: (A) 20% sucrose; (B) 20% trehalose; (C) phosphate buffer pH 6; (D) water; (E) No washing.

Figure 6:
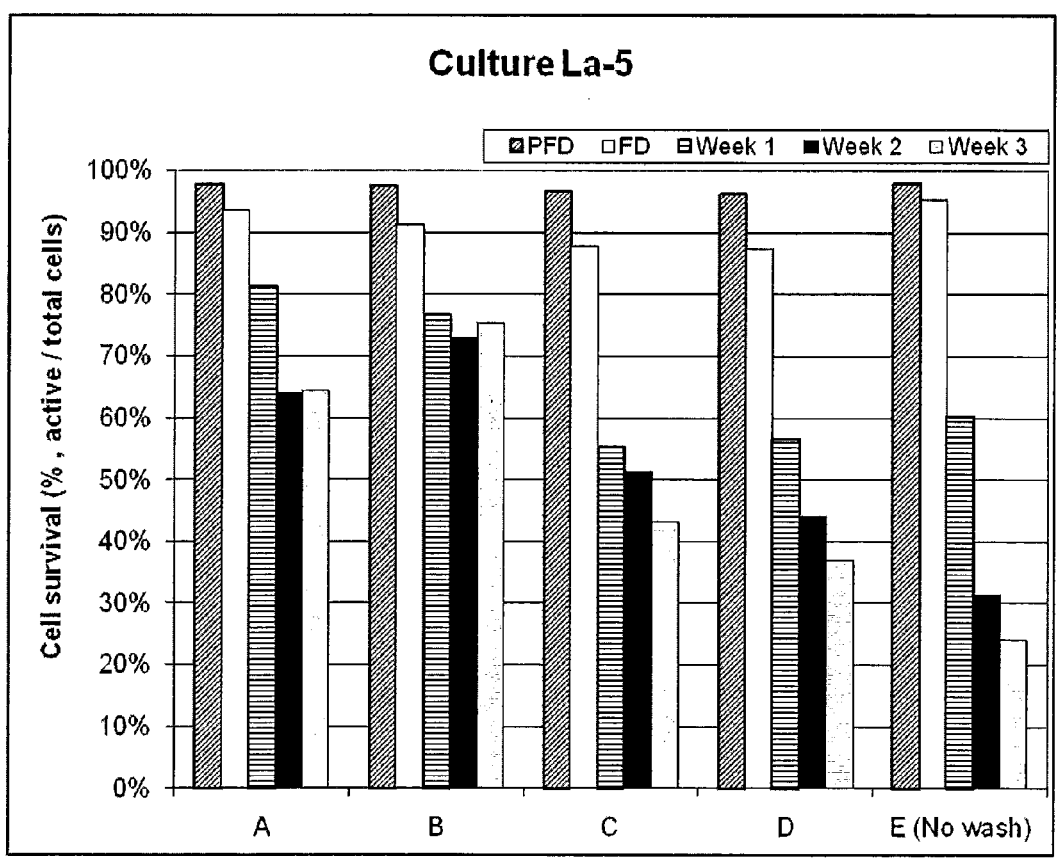

FIG. 6. Culture La-5: Cell survival of frozen (pre-freeze-dried product, PFD) and freeze-dried (FD) products over 3 weeks; storage at 30° C. and Relative Humidity of 30%. Cell survival (%) is the ratio between active cells and total cells. (PFD) pre-freeze-dried product; (FD) Freeze-dried product; Freeze-dried products: (Week 1) 1 week storage; (Week 2) 2 weeks storage; (Week 3) 3 weeks storage. The washing ratio was 2, i.e. 2 volumes washing solution per one volume concentrate. Washing solutions: (A) 20% sucrose; (B) 20% trehalose; (C) phosphate buffer pH 6; (D) water; (E) No washing.

Figure 7:
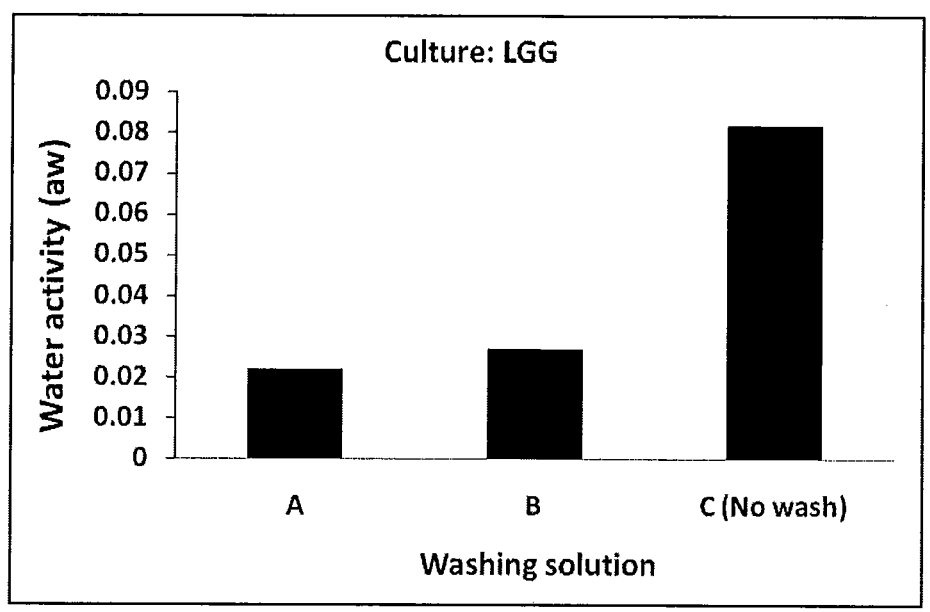

FIG. 7. Culture LGG: Comparison of water activity of freeze-dried products of unwashed (C) and washed cell concentrates with water (B) and 3.4% trehalose (A) at a washing ratio of 2, i.e. 2 volumes washing solution per one volume concentrate.

Figure 8:
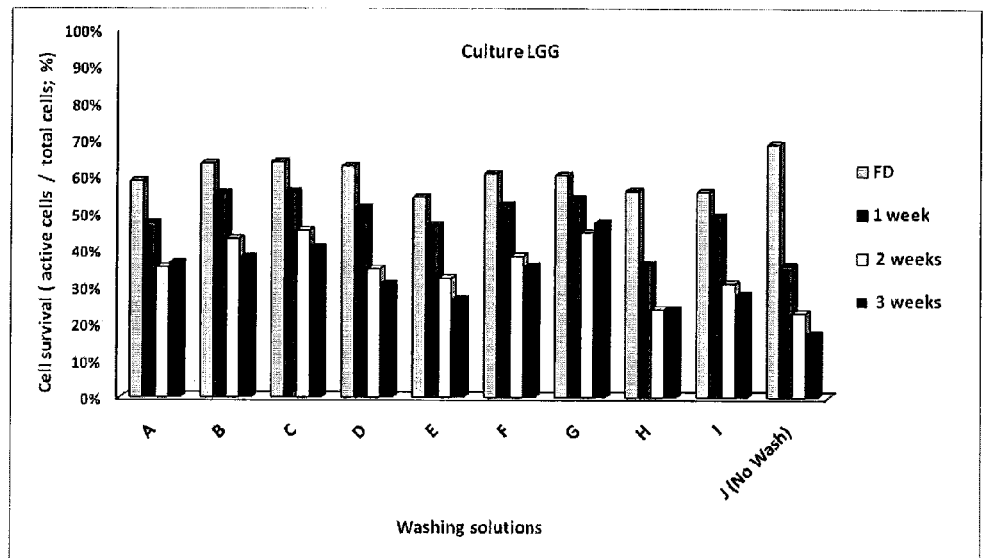

FIG. 8. Culture LGG: Cell survival after freeze-drying and 3 weeks storage at 30° C. and Relative Humidity of 30%. Cell survival (%) is the ratio between active cells and total cells. (FD) freeze-dried product; (Week 1) 1 week storage; (Week 2) 2 weeks storage; (Week 3) 3 weeks storage. (A) Phosphate buffer pH 6; (B) Citrate buffer pH 5; (C) 3.4% Trehalose; (D) 3.4% Sucrose; (E) 0.5% Casein peptone; (F) 0.5% Yeast extract; (G) Peptone-salt solutions; (H) 0.9% NaCl; (I) Water; (J) No wash.

Figure 9:
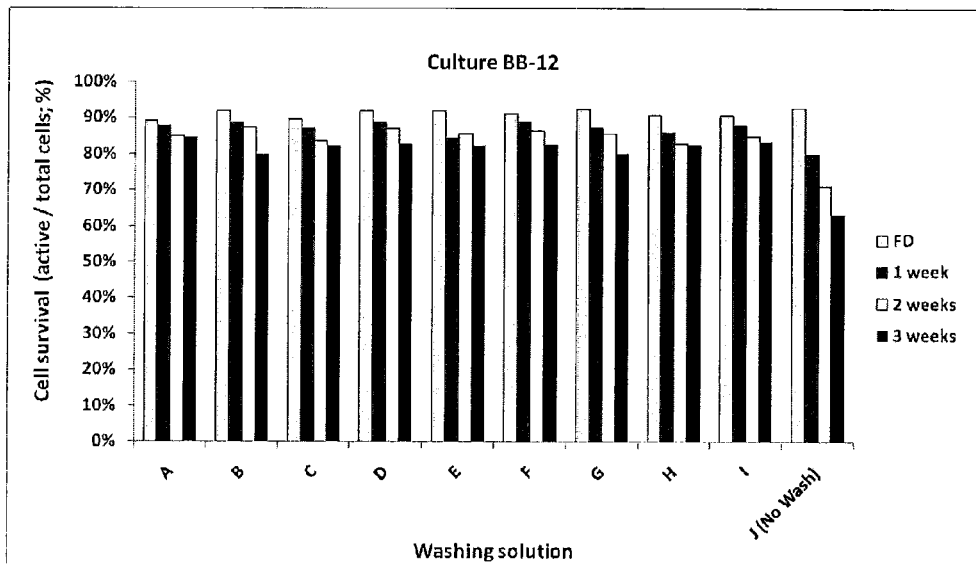

FIG. 9. Culture BB-12: Cell survival after freezing and 3 weeks storage at 30° C. and Relative Humidity of 30%. Cell survival (%) is the ratio between active cells and total cells. (FD) freeze-dried product; (Week 1) 1 week storage; (Week 2) 2 weeks storage; (Week 3) 3 week storage. (A) Phosphate buffer pH 6; (B) Citrate buffer pH 5; (C) 3.4% Trehalose; (D) 3.4% Sucrose; (E) 0.5% Casein peptone; (F) 0.5% Yeast extract; (G) Peptone-salt solutions; (H) 0.9% NaCl; (I) Water; (J) No wash.

Figure 10:
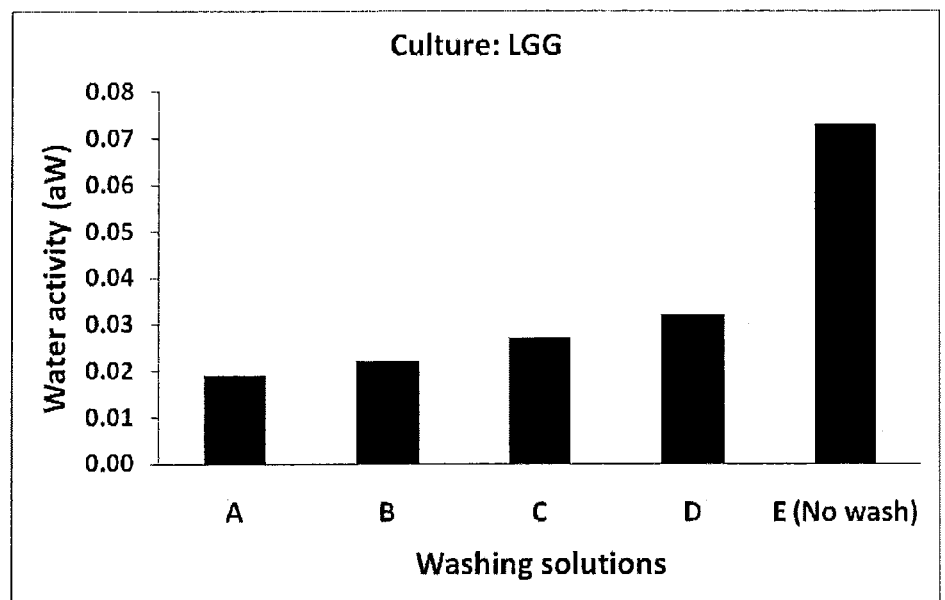

FIG. 10. Culture LGG: Comparison of the water activity of freeze-dried products of unwashed and washed cell concentrates with respect to an effect of different washing solutions on the water activity. The washing ratio was 2, i.e. 2 volumes washing solution per one volume concentrate. Washing solutions: (A) water; (B) 3.4% sucrose; (C) Citrate buffer pH 5 (D) 3.4% trehalose; (E) No washing.

Figure 11:
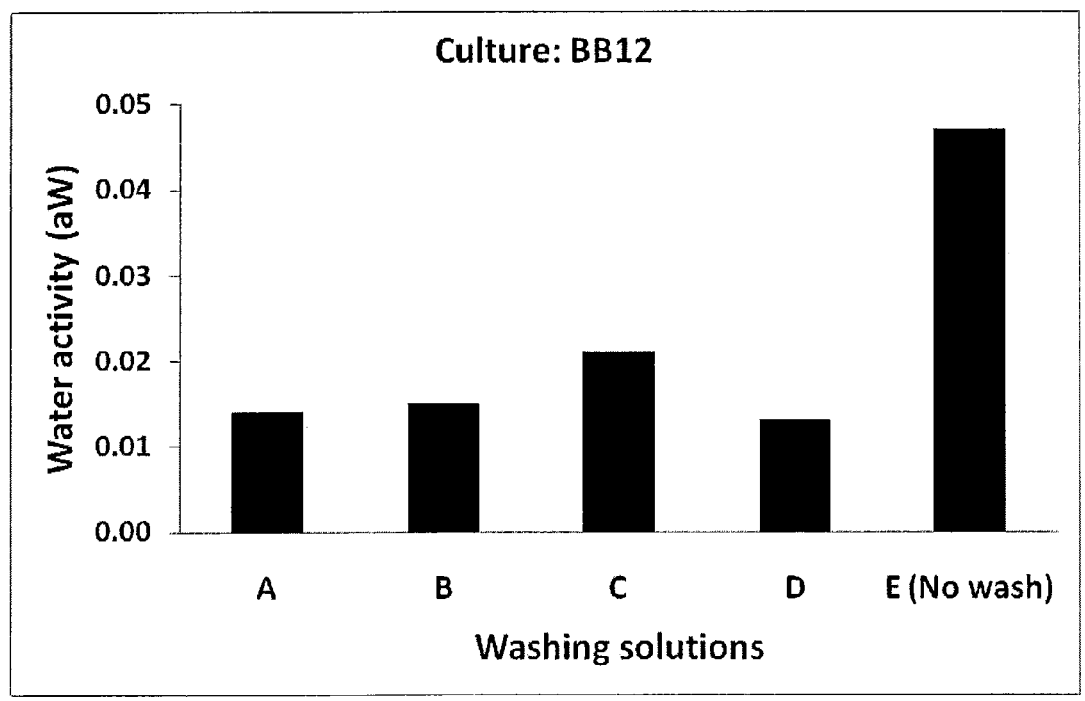

FIG. 11. Culture BB-12: Comparison of the water activity of freeze-dried products of unwashed and washed cell concentrates with respect to an effect of different washing solutions on the water activity. The washing ratio was 2, i.e. 2 volumes washing solution per one volume concentrate. Washing solutions: (A) water; (B) 3.4% sucrose; (C) Citrate buffer pH 5 (D) 3.4% trehalose; (E) No washing.

Figure 12:
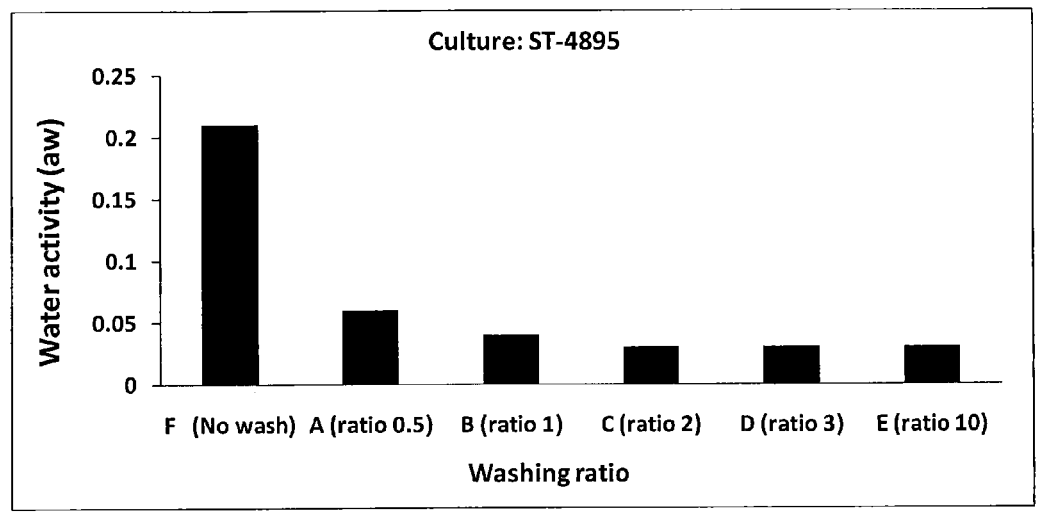

FIG. 12. Culture ST-4895: Comparison of unwashed and washed concentrates with respect to an effect of the washing ratio on the water activity of freeze-dried products. Washing ratio from 0.5 to 10 volumes water per one volume concentrate. (A) washing ratio 0.5; (B) washing ratio 1; (C) washing ratio 2; (D) washing ratio 3; (E) washing ratio 10; (F) No washing.

Figure 13:
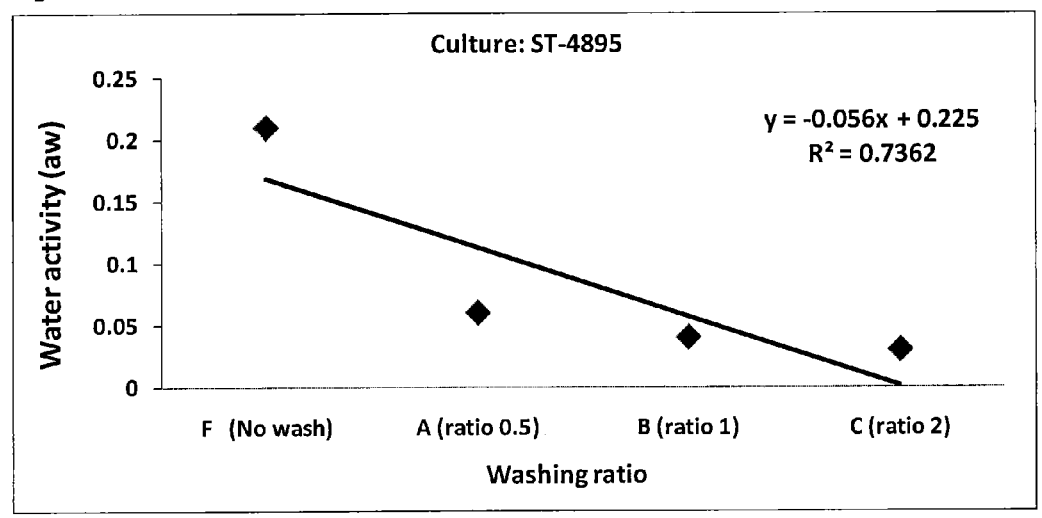

FIG. 13. Culture ST-4895: Relationship between the water activity of freeze-dried products and the washing ratio in a range of 0.5-2 volumes water per one volume concentrate. (A) washing ratio 0.5; (B) washing ratio 1; (C) washing ratio 2; (F) No washing. The line represents the linear fit to the data with a coefficient of determination $R^2$=73. Equation for the linear fit: Y=−0.056*X+0.225.

Figure 14:
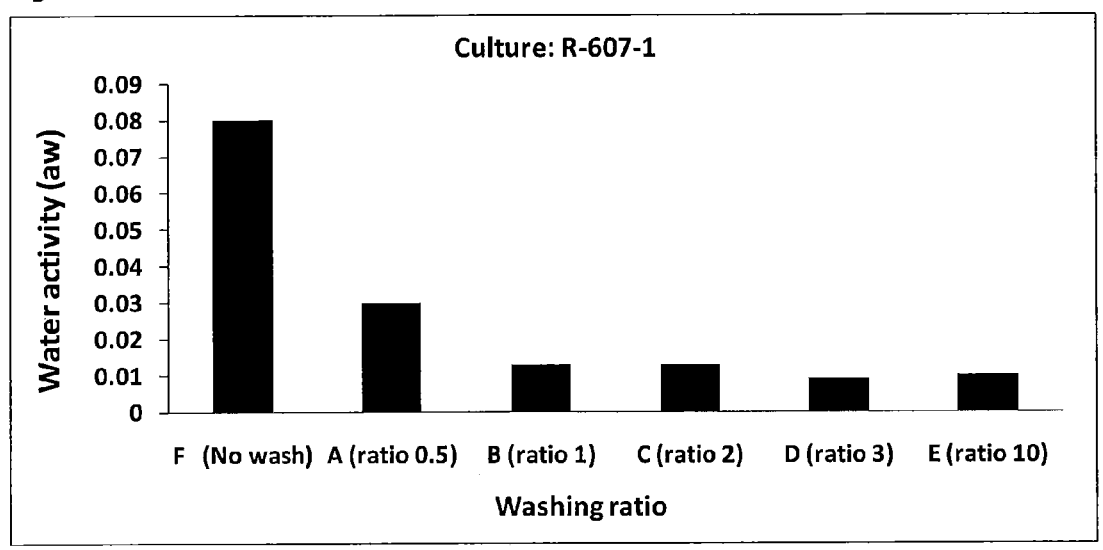

FIG. 14. Culture R-607-1: Comparison of unwashed and washed concentrates with respect to an effect of the washing ratio on the water activity of freeze-dried products. Washing ratio from 0.5 to 10 volumes water per one volume concentrate. (A) washing ratio 0.5; (B) washing ratio 1; (C) washing ratio 2; (D) washing ratio 3; (E) washing ratio 10; (F) No washing.

Figure 15:
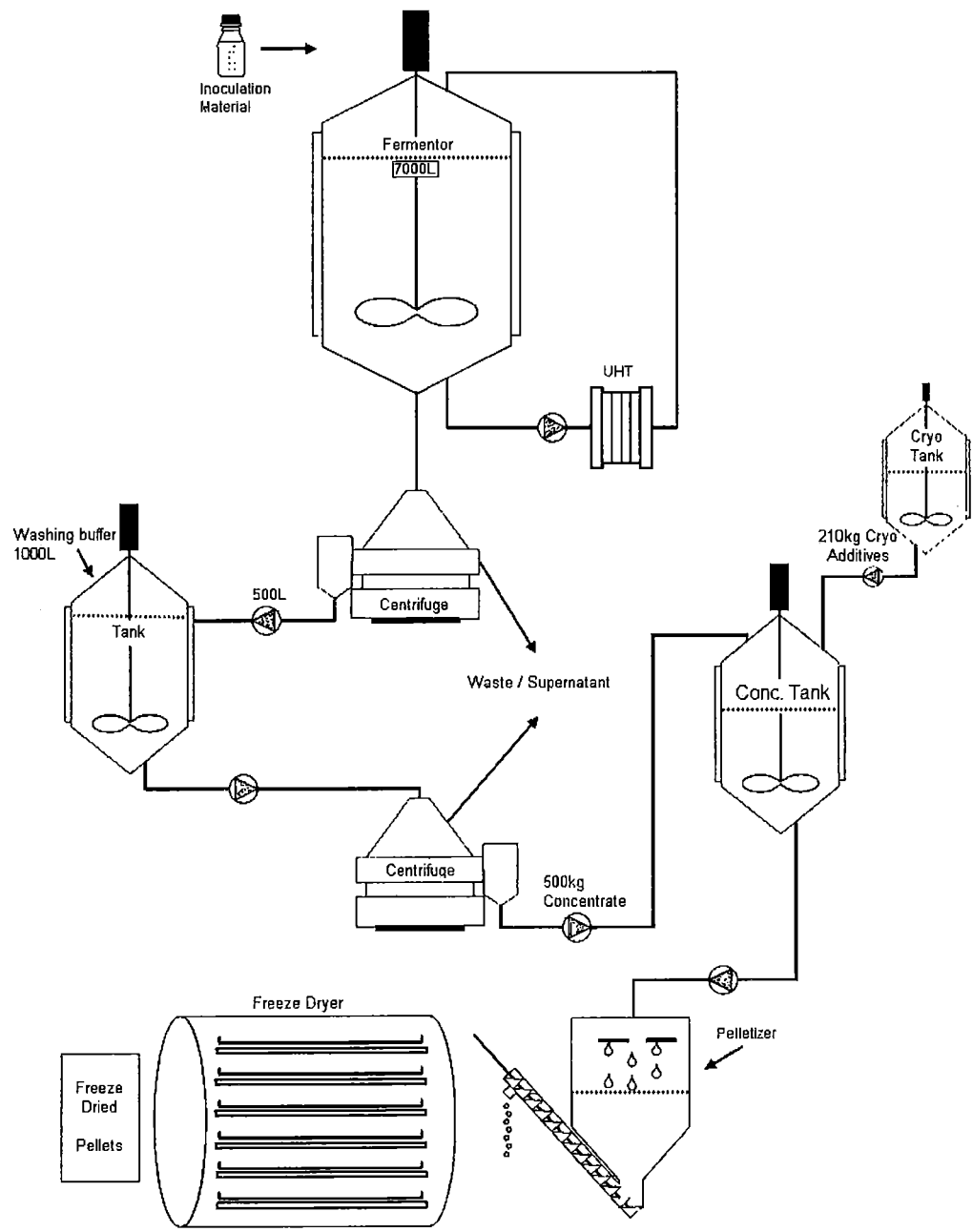

FIG. 15. Process flow diagram of the production. Scale of the production, washing of the cell concentrate, as well as pelletizing and freeze-drying are shown.

Figure 16:
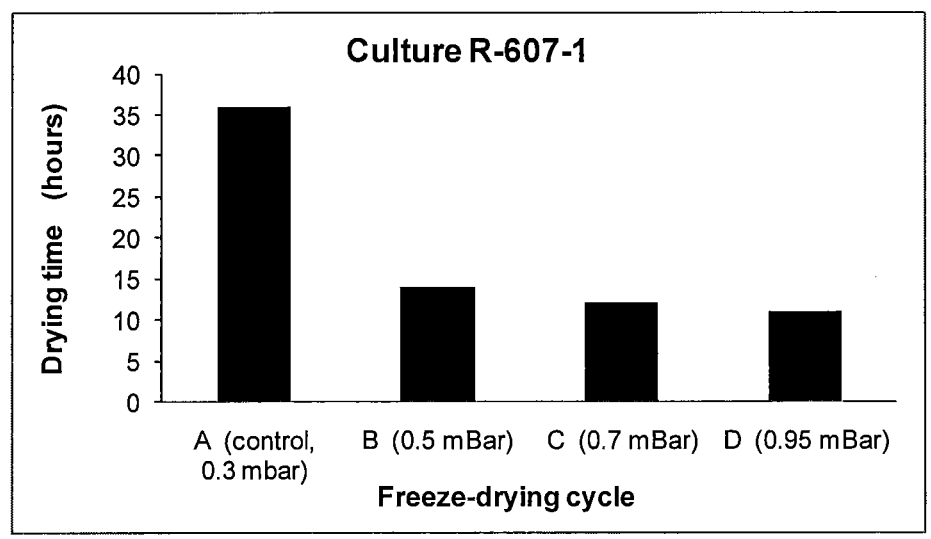

FIG. 16. CultureR-607-1: Comparison of drying times between mild (A) and aggressive conditions (B-D). A (5° C., 0.3 mBar); B (50° C., 0.5 mBar); C (50° C., 0.70 mBar); D (50° C., 0.95 mBar)

Figure 17:
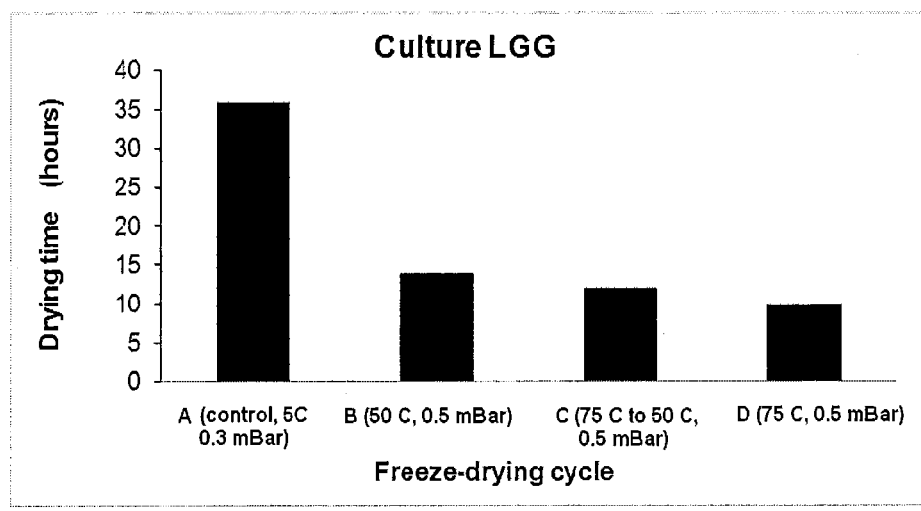

FIG. 17. Culture LGG: Comparison of drying times between mild (A) and aggressive conditions (B-D). A (5° C., 0.3 mBar); B (50° C., 0.5 mBar); C (75° C.→60° C., 0.5 mBar); D (75° C., 0.5 mBar)

EXAMPLES

Example 1

*Bifidobacterium animalis* BB-12: Comparison of Unwashed Vs. Washed Concentrates with Respect to the Effect of the Washing Ratio on Water Activity of Freeze-Dried Products. Water was Used as the Washing Solution The *Bifidobacterium animalis* strain BB-12 was cultivated in MRS medium under standard conditions with controlled pH and temperature during the fermentation in a 700 L reactor, the culture was harvested at early stationary phase and concentrated approx. 14 fold by centrifugation.

After centrifugation, the bacterial concentrate was divided into 6 portions.

5 portions were mixed with water (deionised) in various ratios (ranging from 0.5 to 10) resulting in washed concentrates A-E as given below. The washing was done for 15 min at room temperature using a magnetic stirrer. After washing, the cells were harvested by lab-scale centrifugation (Sorvall RC 6 Plus, Thermo Scientific) for 20 minutes at 10000 g and 4° C. A part of the supernatant was removed after centrifugation in order to obtain the original volume of the concentrate. After that the obtained bacterial concentrate was very well shaken in order to obtain a homogeneous bacterial suspension because the bacterial cells are in the form of a paste at the bottom of the centrifuge tube during the centrifugation. 1 portion was used as a control (concentrate F).

Cryo-protective solution (which consisted of sucrose (15%), maltodextrin (10%) and water (75%)) was added (420 g to 1000 g cell concentrate) to all washed concentrates (A-E) and to the unwashed concentrate (control; F). Subsequently, all bacterial suspensions (A-F) were frozen in liquid nitrogen in a form of pellets (i.e. pre-freeze-dried product, PFD). The PFDs were kept at −50° C. until being freeze-dried.

The following washing ratios were used:

| Portion | Ratio of washing solution (Liters of water per liter of concentrate) |
|---|---|
| A | 0.5 |
| B | 1 |
| C | 2 |
| D | 3 |
| E | 10 |
| F(control) | Unwashed concentrate (No added water) |

The freeze-drying was performed in a Hetosicc freeze dryer, CD-10-1, Heto Lab equipment, Heto-Holten A/S, Allerod, Denmark as described by Kurtmann L, Carlsen C. U., and Skibsted L. H. 265-70. Each PFD (400 g) was put on a drying-tray. Afterwards all PFDs (A-F) were placed in the freeze-drying chamber and dried at the same time as described by Kurtmann et al. (2009), Biotechnol Prog, 25:265-70. Immediately after freeze-drying, the water activity ($a_w$) was measured for all samples. Water activity ($a_w$) of the freeze-dried material was measured at room temperature using an Rotronic HYGROMER® AwVC (Rotronic Instrument Corp., Huntington, N.Y., USA). The range of measurement that was achievable by use of the equipment corresponded to a water activity in the range of 0.03 to 1. Thus, the Limit of Detection (LOD) which is the lowest level that could be detected by the equipment was a water activity of 0.03.

The water activity of all freeze-dried products (A-F) as determined immediately after the freeze-drying process was compared, and the results are presented in FIG. 1.

Results

As can been seen from FIG. 1, although all PFD products (A-F) were dried at the same time in the freeze-drying cabinet, the freeze-dried product of all washed concentrates (A-E) resulted in lower $a_w$ in a range of 0.03-0.12 compared to that of 0.16 for the unwashed concentrate (F).

The results also indicate that there is a threshold washing ratio above which no further improvement in the water activity of freeze-dried product could be obtained by washing the cell concentrate. In this example it was found out that this threshold of the washing ratio is a ratio (volume washing solution/volume concentrate) of about 2 because a higher washing ratio than 2 did not contribute further to a lower water activity of the freeze-dried product.

Moreover, it was found out that a linear correlation exists between the $a_w$, and the washing ratio in the range between 0 and 2 (compare samples A, B, C, and F in FIG. 2). For example, starting from the unwashed concentrate (F) to concentrates that were washed with a ratio of 2, i.e. to the concentrates A, B and C, $a_w$ linearly decreased from 0.16 to 0.03. The line in FIG. 2 represents the linear fit to the data. The linearity is satisfactory with $R^2$ of 89.6%.

In conclusion, these results show that:
Washing of the cell concentrate increases the drying efficiency, and thus washed cell concentrates of BB-12® dried better compared to unwashed concentrate using the same drying conditions and drying time. Thereby, washing resulted in a significantly lower water activity ($a_w$) compared to the sample without washing.

A threshold washing ratio exists. This threshold ratio is 2 in the present experiment because a higher washing ratio than 2 did not contribute further to a lower water activity of the freeze-dried product.

A linear correlation exists between $a_w$ and the washing ratio when the washing ratio is between 0 and 2 (i.e. 2 liters water per liter concentrate).

Example 2

*Lactobacillus rhamnosus* LGG: Comparison of Unwashed Vs. Washed Concentrates with Respect to the Effect of the Washing Ratio on the Water Activity of Freeze-Dried Products. Water was Used as the Washing Solution The LGG® was cultivated in MRS medium under standard conditions with controlled pH and temperature during the fermentation in a 700 L reactor. The culture was harvested at early stationary phase and concentrated approx. 14 fold by centrifugation. After centrifugation, the bacterial concentrate was divided into 6 portions, washed with deionized water, and a cryo-protective solution was added as described in Example 1. Freeze-drying and water activity measurements were performed as described in Example 1.

Results

The experiment presented in this example is identical to that given in Example 1 except that it was carried out with another bacterial culture, i.e. the *Lactobacillus rhamnosus* LGG. The results are presented in FIG. 3.

The results of this experiment are in agreement with the findings described in Example 1, i.e. that the freeze-dried product of all washed cell concentrates (A-E) resulted in lower $a_w$ compared to unwashed concentrate (F). The water activity for washed concentrates (case A-E) was in the range of between 0.045 and 0.12 compared to 0.13 for the control i.e. the unwashed concentrate (F) (FIG. 3).

These results also confirm the finding described in Example 1 that there is a threshold washing ratio above which no further improvement of the water activity of freeze-dried product can be obtained by washing the cell concentrate, and that this threshold washing ratio is 2.

As in Example 1, it was found that a linear correlation between $a_w$ and the washing ratio exists in the washing ratio range of between 0 and 2 (A, B, C, and F'; see FIG. 4). For example, starting from unwashed concentrate (F) to the washed concentrates (A, B and C), $a_w$ linearly decreased from 0.13 to 0.045. The line in FIG. 4 represents the linear fit to the data. The linearity is satisfactory with $R^2$ of 93.6%.

In conclusion, the results for LGG® given in this experiment confirm all findings presented in Example 1.
  Washing the cell concentrates increases drying efficiency, thus resulting in lower water activity in the washed, freeze-dried products compared to freeze-dried products of unwashed culture concentrates.
  A threshold washing ratio exists. This threshold ratio is 2 in the present experiment, because a higher washing ratio than 2 did not contribute further to a lower water activity of the freeze-dried product.
  A linear correlation exists between $a_w$ and the washing ratio when the washing ratio is between 0 and 2 (i.e. 2 liters water per liter concentrate).

Example 3

*Lactobacillus acidophilus* LA-5: Comparison of Freeze-Dried Products of Washed and Unwashed Cell Concentrates with Respect to Five Different Washing Solutions The culture La-5 was cultivated in MRS medium under standard conditions with controlled pH and temperature during the fermentation, in a 700 L reactor. The culture was harvested at early stationary phase and concentrated approx. 14 fold by centrifugation.

After centrifugation, the bacterial concentrate was divided into 5 portions. 4 portions were mixed with a particular washing solution (see table below), i.e. one volume of concentrate was mixed with two volumes of washing solution as given below (A, B, C, D). 1 portion was used as control (unwashed concentrate E).

The washing process, addition of cryo-protective solution, freeze-drying, and water activity measurements were performed as described in Example 1. The following washing solutions were used:

| Portion | Ratio of washing solution to culture concentrate | Washing solution |
|---|---|---|
| A | 2 | 20% (w/w) Sucrose in water |
| B | 2 | 20% (w/w) Trehalose in water |
| C | 2 | Phosphate buffer (pH = 6) |
| D | 2 | Water (deionised water) |
| E | | No wash (Control) |

In order to study the stability of the product with respect to cell viability during storage, freeze-dried products were stored at 30° C. and a relative humidity of 30% for 1, 2 and 3 weeks. Subsequently, samples were taken out for Flow cytometry analysis as described in WO 2006/125446.

The flow cytometry method was used to quantify active versus inactive cells on the level of energy metabolism. Active cells, i.e. the number of viable cells per gram sample, are detected by a cellular fluorescence staining, which differentiates cells generating a membrane potential from cells without such functional energy metabolism as described. In the text:
  Active cells refer to number of viable cells per gram sample
  Total cells refer to sum of active and inactive cells
  Cell survival refers to % of active cells relative to total cells Results 3.1:
Comparison of the Water Activity of Freeze-Dried Products of Washed and Unwashed Cell Concentrates with Respect to Different Washing Solutions The aim of this example was to study the effect of different washing solutions on the water activity of washed freeze-dried products compared to that of unwashed freeze-dried products. In this example, a cell concentrate of a culture of La-5 was used. A washing ratio of 2 (i.e. 2 volumes washing solution per volume concentrate) was selected in order to provide more profound data on potential synergetic effects of the washing ratio and the type of washing solution.

The water activities of all freeze-dried (FD) products (A-E), as determined immediately after the freeze-drying process were compared. The results are presented in FIG. 5. Although different washing solutions were used, all washed FD products (A-D) resulted in a lower $a_w$ of 0.03-0.04 as compared to that of 0.08 of unwashed FD product (case E). All PFD products were dried at the same time in the freeze-dryer.

Moreover, the cell concentrate washed with water (D) resulted in a FD product with an $a_w$ of 0.03 which is comparable to the water activity (0.03-0.04) of freeze-dried products washed with sucrose solution (A), trehalose solution (B) or phosphate buffer (C). This demonstrates that the major effect on obtaining a low $a_w$ for the FD product comes from the washing process itself and not from the particular washing solution used.

Results 3.2:
Cell Survival in Washed and Unwashed Cell Concentrates of Strain La-5 During Storage Results for cell survival, i.e. the % of active relative to total (active plus inactive) cells, of all FD products of La-5 after freeze-drying and 1, 2 and 3 weeks storage at 30° C. and a relative humidity of 30% are summarized in FIG. 6. The cell survival of all FD products after freeze-drying is near 90%. A significant drop in cell survival of about 31-35% occurred after 1 week storage for FD products washed with phosphate buffer (C) and with water (D) as well as for unwashed FD product (E). The lowest cell survival of 24% after 3 weeks of storage was obtained for the unwashed FD product (case E), for which cell survival was 40% and 51% lower compared with the highest cell survival obtained by washing the cell concentrate with sucrose solution (B) or trehalose solution (A).

These results confirm the findings in Example 5 demonstrating that washing of the cell concentrate results in a higher survival during long-term storage, and that some washing solutions like sucrose and trehalose are more efficient as compared to others with respect to preserving the cell viability during washing and subsequent freeze-drying and storage.

Overall, the conclusions that can be drawn from the results presented in Example 3 with cultures of the strain La-5 are:

- Washing of the cell concentrate increases the drying efficiency, thus resulting in a lower water activity in washed freeze-dried products compared to freeze-dried products of unwashed culture concentrate. This finding is in agreement with the results given in Examples 1 and 2.
- The low water activity of washed FD products compared to unwashed FD products is due to the effect of the washing process itself, and is not attributable to the effect of a particular washing solution used.
- Compared to the unwashed FD product, the washing with some particular solutions such as sucrose and trehalose results not only in a lower water activity of the FD products but also in more stable FD products with respect to preserving cell viability during storage.

Example 4

Lactobacillus rhamnosus LGG: Comparison of the Water Activity of Freeze-Dried Products of Washed and Unwashed Cell Concentrates with Respect to Different Washing Solutions, i.e. Water and Trehalose Solution The *Lactobacillus rhamnosus* strain LGG was cultivated in 800 liters MRS medium under standard conditions with controlled pH and temperature. The culture was harvested at early stationary phase and concentrated approx. 13 fold by centrifugation.

The bacteria-containing concentrate was divided into 3 portions, each comprising a volume of 20 liters. For two of the portions, the bacteria-containing culture concentrate (20 liters) was pumped into a tank, and 40 liters of deionized water (A) or 3.4% trehalose (B) were added. The resulting suspension was agitated, and concentrated to 20 liters using a centrifuge (CSA-6, Westfalia).

The following washing solutions were used:

| Portion | Ratio of washing solution to culture concentrate | Washing solution |
| --- | --- | --- |
| A | 2 | Water (deionised water) |
| B | 2 | 3.4% (w/w) Trehalose in water |
| C | 2 | No wash (Control) |

After that, 10 liters of each washed concentrate (A and B) were mixed with cryo-protective solution as described in Example 1 above. One portion was used as a control (concentrate C).

The addition of cryo-protective solution was performed as described in Example 1. Afterwards all bacterial suspensions (A-C) were frozen in liquid nitrogen in the form of pellets (i.e. pre-freeze-dried products, PFD). The PFDs were kept at −50° C. until being freeze-dried.

The freeze-drying was performed as described in Example 1 with the following modifications: In total three freeze-dryings were carried out, i.e. one for each PFD bulk, as described previously by Kurtmann L et al. (2009), Biotechnol Prog. 25(1):265-70. Each freeze-drying was carried out for 22 hours with a PFD load in the drying cabinet of 10 kg. The water activity of each FD product was measured immediately after freeze-drying.

The water activity measurement was performed as described in Example 1.

Results

The aim of this example was to study the effect of two different washing solutions on the water activity of washed freeze-dried products compared to that of unwashed freeze-dried product. In this example, the cell concentrate of a culture of strain LGG was used. A washing ratio of 2 was chosen in order to provide more profound data on potential synergetic effects of the washing ratio and the washing solution.

The water activity of all freeze-dried (FD) products (A-C), as determined immediately after the freeze-drying process was compared. The results are presented in FIG. 7. The FD product washed with trehalose solution (B) had a similar $a_w$ (0.027) compared to that of the FD product washed with water ($a_w$=0.022; A). Thus, both washed FD products (A and B) resulted in an $a_w$ below the Limit of Detection (LOD) of 0.03 for the equipment indicating that the samples were much more dried compared to the unwashed FD product ($a_w$=0.08; C), although they had been freeze-dried for the same duration. In conclusion, these results are in agreement with the conclusions made in Examples 1; 2; and 3 above which found that:

- Washing of a cell concentrate results in a lower water activity in FD products as compared to unwashed FD product when the FD products are freeze-dried under the same drying conditions and for the same time.
- The low water activity of washed FD products compared to unwashed FD products is due to the washing process itself, and is not attributable to the effect of a particular washing solution used.

Example 5

Cultures BB12 and LGG: Cells Washed with Nine Different Washing Solutions

The experiment was performed for cultures of the strains BB-12 and LGG. The bacteria-containing concentrate of BB-12 and LGG was made as described in Examples 1 and 2, respectively. After centrifugation, one volume of concentrate BB-12 or LGG was mixed with two volumes washing solution. In total, 9 different washing solutions were used as described below (A-I, Table 1). One portion was used as a control (concentrate J).

The washing process, addition of cryo-protective solution, and freeze-drying were performed as described in Example 1.

The stability of freeze-dried formulations (A-J) was then evaluated with respect to the cell viability during storage for 1, 2 and 3 weeks at 30° C. with a relative humidity of 30%. After that, samples were taken out for Flow cytometry analysis as described in Example 3.

TABLE 1

Washing solutions

| Portion | Solutions | pH |
|---|---|---|
| A | Phosphate buffer | 6.1 |
| B | Citrate buffer | 5.04 |
| C | 3.4% Trehalose | 6.54 |
| D | 3.4% Sucrose | 6.43 |
| E | 0.5% Casein peptone | 6.78 |
| F | 0.5% Yeast Extract | 5.86 |
| G | Peptone Saline Diluent | 6.9 |
| H | NaCl | 6.37 |
| I | Water (deionised water) | 6.10 |
| J | No wash | |

Results

The aim of this example was to study the effect of different washing solutions with respect to preserving cell viability (cell survival) during freeze-drying and storage at 30° C. with a relative humidity of 30%. A washing ratio of 2 was chosen in order to provide more profound data on potential synergetic effects of the washing ratio and the washing solution. Nine different washing solutions, including water, were tested as shown in Table 1. The results of cell survival of freeze-dried product after freeze-drying (FD) and after 1, 2 and 3 weeks storage at 30° C. with a relative humidity of 30% are presented in FIG. 8 for LGG and FIG. 9 for BB12.

For LGG, a decrease in cell survival was already seen after storage for 1 week. The most significant cell loss of 33% occurred with the unwashed concentrate (J), followed by 20% cell loss with concentrate washed with NaCl (0.9%) (H). For all FD products (A-J), the cell survival after 2 weeks of storage was similar to that after 3 weeks. The lowest cell survival of 17% after 3 weeks of storage was obtained with the unwashed concentrate (3), which was 31% lower compared with the highest cell survival obtained by washing the concentrate with peptone saline solution (48%) (G). The second highest cell survival of 41% was obtained by washing with trehalose solution (C) which was still significantly higher, i.e. 21%, in comparison with the unwashed FD product (J). Washing with water (I) also resulted in a 11% higher cell survival after 3 weeks storage compared to the unwashed FD product (J). For BB-12, as shown in FIG. 9, the cell survival for all FD products after freeze-drying (A-J) was about 90%. Cell survival after 3 weeks of storage was in the range of 80-85%. The lowest cell survival of 62-63% after 3 weeks of storage was obtained with the unwashed concentrate (J), and this survival was in the range of 10-23% lower compared to the other washed FD products (A-I).

In summary, the results from these experiments with both cultures of LGG® and BB-12® demonstrate that washing of the cell concentrate results in higher cell survival during long-term storage. Moreover, the difference seen in cell survival after 3 weeks storage also indicates that certain washing solutions are more effective than others with respect to preserving cell viability during washing and subsequent freeze-drying and storage.

Example 6

*Lactobacillus rhamnosus* LGG: Comparison of the Water Activity of Freeze-Dried Products of Washed and Unwashed Cell Concentrates with Respect to 4 Different Washing Solutions The culture LGG was cultivated in MRS medium under standard conditions with controlled pH and temperature during fermentation, in a 700 L reactor. The culture was harvested at early stationary phase and concentrated approx. 14 fold by centrifugation.

After centrifugation, the bacterial concentrate was divided into 5 portions. 4 portions were mixed with a particular washing solution (see table below). In particular, one volume of concentrate was mixed with two volumes of washing solution as shown in the Table below (A, B, C, D). One portion was used as a control (unwashed concentrate E).

The washing process, addition of cryo-protective solution, freeze-drying, and water activity measurement was performed as described in Example 1.

The following washing solutions were used

| Portion | Ratio of washing solution to culture concentrate | Washing solution |
|---|---|---|
| A | 2 | Water (deionised water) |
| B | 2 | 3.4% (w/w) sucrose in water |
| C | 2 | Citrate buffer (pH = 5) |
| D | 2 | 3.4% (w/w) trehalose in water |
| E | | No wash (Control) |

Results

The aim of Example 6 was to study the effect of 4 different washing solutions on the water activity of washed freeze-dried products compared to that of unwashed freeze-dried product. In this example, a cell concentrate of a culture of the strain LGG was used. A washing ratio of 2 (2 volumes washing solution per volume concentrate) was chosen in order to provide more profound data on potential synergetic effects of the washing ratio and the washing solution.

The water activity of all freeze-dried (FD) products (A-E), as determined immediately after the freeze-drying process was compared. The results are presented in FIG. 10. Although different washing solutions were used, all washed FD products (A-D) resulted in very low $a_w$ of less than 0.03 compared to that of 0.072 of unwashed FD product (case E). All PFD products were dried at the same time in the freeze-dryer. In addition, all washed FD products (A-D) resulted in $a_w$ below the Limit of Detection (LOD) of 0.03 for the equipment indicating that the samples were more dried compared to the unwashed sample (E). This demonstrates that the strong effect on obtaining a low $a_w$ for the FD product comes from the washing process itself and is not attributable to the particular washing solution used.

In conclusion, these results are in agreement with the conclusions made in Examples 1; 2; 3; 4 and 7 which found that:

Washing of the cell concentrate results in a lower water activity in FD products as compared to unwashed FD product when both have been freeze-dried under the same drying conditions and duration.

A low water activity of washed FD products compared to that of unwashed FD products is due to the effect of the washing process itself, and not attributable to the effect of a particular washing solution that is used.

Example 7

*Bifidobacterium culture*, 88-12: Comparison of the Water Activity of Freeze-Dried Products of Washed and Unwashed Cell Concentrates with Respect to 4 Different Washing Solutions A culture of the strain BB-12 was cultivated in MRS medium under standard conditions with controlled pH and temperature during the fermentation, in a 700 L reactor. The culture was harvested at early stationary phase and concentrated approx. 14 fold by centrifugation.

After centrifugation, the bacterial concentrate was divided into 5 portions. 4 portions were mixed with a particular washing solution (see table below). In particular, one volume of concentrate was mixed with two volumes of washing solution as given below (A, B, C, D). One portion was used as a control (unwashed concentrate E).

The washing process, addition of cryo-protective solution, freeze-drying, and water activity measurement were performed as described in Example 1.

The following washing solutions were used

| Portion | Ratio of washing solution to culture concentrate | Washing solution |
| --- | --- | --- |
| A | 2 | Water (deionised water) |
| B | 2 | 3.4% (w/w) sucrose in water |
| C | 2 | Citrate buffer (pH = 5) |
| D | 2 | 3.4% (w/w) trehalose in water |
| E | | No wash (Control) |

Results

The aim of example 7 was to study the effect of different washing solutions on the water activity of washed freeze-dried products compared to that of unwashed freeze-dried product. Thus, a washing ratio of 2 (i.e. 2 volumes washing solution per volume concentrate) was chosen in order to provide more profound data on potential synergetic effects of the washing ratio and the washing solution. The experiment presented in this example was identical to that described in Example 6 except that it was carried out with another culture of BB-12.

The water activity of all freeze-dried (FD) products (A-E), as determined immediately after the freeze-drying process was compared, and the results are presented in FIG. 11. Although different washing solutions were used, all washed FD products (A-D) resulted in a lower $a_w$ in the range of 0.013-0.021 as compared to that of 0.047 of unwashed FD product (E). All PFD products were dried at the same time in the freeze-dryer. In addition, all washed FD products (A-D) resulted in an $a_w$ below the Limit of Detection (LOD) of 0.03 for the equipment indicating that the samples were more dried compared to the unwashed sample (E). This also demonstrates that the main effect on obtaining a low $a_w$ for FD product comes from the washing process itself and not the particular washing solution used.

In conclusion, these results are in agreement with the conclusions made in Examples 1; 2; 3; 4 and 6 which described that:

Washing of cell concentrates results in a lower water activity in the FD product compared to unwashed FD product when both have been freeze-dried under the same drying conditions and time.

The low water activity of washed FD products compared to unwashed FD products is due to the effect of washing process itself, and not attributable to the effect of the particular washing solution used.

Example 8

*Streptococcus thermophilus*, ST-4895: Comparison of Unwashed and Washed Concentrates with Respect to Effect of Washing Ratio on Water Activity of Freeze-Dried Products. Phosphate Buffer (pH 6) was Used as the Washing Solution The strain ST-4895 was cultivated in MRS medium under standard conditions with controlled pH and temperature during the fermentation in a 700 L reactor. The culture was harvested at early stationary phase and concentrated approx. 14 fold by centrifugation. After centrifugation, the bacterial concentrate was divided in 6 portions. Five portions (A-E) were washed with phosphate buffer (pH 6) and 1 portion was used as a control (unwashed concentrate F) as described in Example 1.

Addition of cryo-protective solution was performed as described in Example 1.

Freeze-drying was performed as described in Example 1 with the following modification: a pressure of 0.5 mBar was used instead of 0.3 mBar. Water activity measurement was performed as described in Example 1.

Results

The experiment presented in this example was identical to that described in Examples 1, 2 and 9 except that it was carried out with another culture, i.e. a culture of the strain ST-4895, and that phosphate buffer with pH 6 was used as a washing solution. The results are presented in FIGS. 12 and 13.

Although a different washing solution, i.e. phosphate buffer at pH 6, was used compared to water used in Examples 1 and 2, and the peptone saline diluent used in Example 9, the results in this example are in agreement with the findings in the above Examples (1, 2 and 9). Specifically, the freeze-dried product of all washed cell concentrates (A-E) had a lower $a_w$ as compared to the unwashed concentrate (F). All PFD products were dried at the same time in the freeze-dryer. The water activity of the washed concentrates (A-E) was in the range of 0.03-0.6 compared to 0.22 for the control, i.e. the unwashed concentrate (F) (FIG. 12).

Although phosphate buffer pH 6 was used as a washing solution in this example, all washed FD products (A-E) had a very low $a_w$ (0.03-0.06) which confirms the above results obtained with freeze-dried products washed with water (A-E) in Examples 1 and 2; and with peptone saline diluent in Example 9. These results are also in agreement with the findings presented in examples 3, 4 6 and 7 which showed that the main effect on obtaining a low $a_w$ in FD products comes from the washing process itself and not from the particular washing solution used.

Although phosphate buffer pH 6 was used as a washing solution in this example, the results also confirm the findings in Examples 1, 2 and 9 that there is a threshold washing ratio above which no further improvement in water activity of freeze-dried product will be obtained by washing the cell concentrate, and that this threshold washing ratio is 2. This demonstrates that the threshold washing ratio of 2 does not depend on the particular washing solution used, but it is due to the washing process itself.

As in Examples 1, 2 and 9, it was found out that a linear correlation exists between $a_w$ and the washing ratio in the range of 0 to 2 (A, B, C, and F) (FIG. 13). For example, starting from the unwashed concentrate (F) to concentrate that was washed with a washing ratio of 2 (A, B and C), the $a_W$ linearly decreased from 0.22 to 0.03. The line in FIG. 13 represents the linear fit to the data. Linearity is satisfactory with $R^2$ of 73.6.

In conclusion, the results for ST-4895 described in this experiment confirm all findings presented in Examples 1; 2 and 9.

Washing the cell concentrate increases the drying efficiency, thus resulting in a lower water activity in washed freeze-dried products compared to freeze-dried product of unwashed culture concentrate.

A threshold washing ratio exits and is 2 in this experiment; A higher washing ratio than 2 does not contribute further to decreasing the water activity of freeze-dried product.

The threshold washing ratio of 2 does not depend on the washing solution used, but it is due to the washing process itself.

A linear correlation exists between $a_w$ and the washing ratio as starting from unwashed to concentrates that were washed with a washing ratio of 2 (i.e. 2 liters water per liter concentrate).

The low water activity of washed FD products compared to unwashed FD products is due to an effect of the washing process itself, and not to the effect of a particular washing solution used, which is in agreement with the findings presented in examples 3, 4, 6 and 7.

Example 9

*Lactococcus Lactis*, R-607-1: Comparison of Unwashed and Washed Concentrates with Respect to Effects of the Washing Ratio on the Water Activity of Freeze-Dried Products. Peptone Saline Diluent (pH 6.9) was Used as the Washing Solution The strain R-607-1 was cultivated in MRS medium under standard conditions with controlled pH and temperature during the fermentation in a 700 L reactor. The culture was harvested at early stationary phase and concentrated approx. 14 fold by centrifugation. After centrifugation, the bacterial concentrate was divided into 6 portions. Five portions (A-E) were washed with peptone saline diluent (pH 6.9) and 1 portion was used as a control (unwashed concentrate F) as described in Example 1.

Addition of cryo-protective solution was performed as described in Example 1.

Freeze-drying was performed as described in Example 1 with the following modification: a pressure of 0.5 mBar was used instead of 0.3 mBar. The water activity measurement was performed as described in Example 1.

Results

The experiment presented in this example was identical to that described in Examples 1, 2 and 8 except that it was carried out with another culture, i.e. a culture of the strain R-607-1, and that peptone saline diluent (pH 6.9) was used as washing solution. The results are presented in FIG. 14.

Although a different washing solution, i.e. peptone saline diluent (pH 6.9), was used (and not water as in Examples 1 and 2, or phosphate buffer at pH 6 as in Example 8), the results in this example are in agreement with the findings in the above Examples (1, 2 and 8), i.e. the freeze-dried product of all washed cell concentrates (A-E) had a lower $a_w$ compared to unwashed concentrate (F). All PFD products were dried at the same time in the freeze-dryer. Water activity of washed concentrates (A-E) was equal or below ≤0.03 compared to an $a_w$ of 0.08 of the control, i.e. the unwashed concentrate (F) (FIG. 14). In addition, washed FD products (B-D) had an $a_w$ below the Limit of Detection (LOD) of 0.03 for the equipment indicating that the samples were more dried compared to the unwashed sample (F). This also confirms the findings presented in examples 3, 4 6 and 7 that the main effect on obtaining a low $a_w$ for FD product results from the washing process itself and not from the particular washing solution used.

Although peptone saline diluent (pH 6.9) were used as washing solution in this example, the results also confirm the findings in Examples 1, 2 and 8 that there is a threshold washing ratio above which no further improvement in water activity of the freeze-dried product will be obtained by washing the cell concentrate, and that this threshold washing ratio is 2. This demonstrates that the threshold washing ratio of 2 does not depend on the washing solution used, but is due to the washing process itself.

In conclusion, the results for R-607-1 given in this example confirm all findings presented in Examples 1; 2 and 8.

Washing of the cell concentrates increases the drying efficiency, thus resulting in a lower water activity in washed freeze-dried products compared with dried product of unwashed culture concentrate.

A threshold washing ratio exits and is 2; as higher washing ratio than 2 does not contribute further to a lower water activity of a freeze-dried product.

The threshold washing ratio of 2 does not depend on the washing solution used, but it is due to the washing process itself.

The low water activity of washed FD products compared to unwashed FD products is due to the effect of the washing process itself, and not to the effect of a particular washing solution used in agreement with the findings of Examples 3, 4, 6 and 7.

Example 10

*Lactobacillus rhamnosus* LGG: Comparison of Product Appearance and Water Activity of Freeze-Dried Products of Washed and Unwashed Products when Freeze-Dried at Different Pressure The strain LGG was cultivated in 800 liters MRS medium under standard conditions with controlled pH and temperature. The culture was harvested at early stationary phase and concentrated approx. 13 fold by centrifugation.

The concentrated culture was divided into 2 portions of 20 liters each. One of the portions of the culture concentrate (20 liters) was pumped into a tank, and 40 liters of deionized water (A) were added. The resulting suspension was agitated and concentrated to 20 liters using a centrifuge (CSA-6, Westfalia) resulting in a washed concentrate (A). The second portion was used as control i.e. unwashed concentrate (concentrate B).

The addition of cryo-protective solution was performed as described in Example 1. Afterwards both bacterial suspensions (A-B) were frozen by liquid nitrogen in the form of pellets (i.e. PFD). The PFDs were kept at −50° C. until being freeze-dried.

The following washing solutions were used

| Portion | Ratio of washing solution to culture concentrate | Washing solution |
| --- | --- | --- |
| A | 2 | Water (deionised water) |
| B | 2 | No wash (Control) |

The freeze-drying was performed as described in Example 1 with the following modifications. Pre-freeze-dried product (PFD) was dried at five different chamber pressures (0.3; 0.5; 0.7; 0.9 and 1.2 mBar). One particular chamber pressure was used per freeze-drying, so in total five freeze-dryings were done per PFD product (A and B). 4000 g PFD were used per drying.

Water activity measurement ($a_w$) of each FD product (A and B) was performed immediately after freeze-drying as described in Example 1.

After freeze-drying under various chamber pressures, the freeze-dried products were visually assessed for product appearance, which was done by a visual comparison to a reference. As a reference, a freeze-dried product of unwashed concentrate (portion B) which was freeze-dried at a pressure of 0.3 mBar was used.

The following categorization was used for evaluation of freeze-dried product appearance after freeze-drying:

0 refers to products similar to the reference, i.e. normal pellet shape 1 refers to product with a less normal pellet shape 2 refers to product with bad pellet shape 3 refers to product with complete loss of pellet shape Results Evaluation of freeze-dried products normally includes the observation of the product appearance after freeze-drying. One of the desired characteristics of freeze-dried products includes avoiding changes in the fried-product product appearance. Thus, the aim of this example was to study the effect of washing on product appearance when products undergo freeze-drying at various pressures. Two types of pre-freeze-dried products (PFDs: A-B) were used. The first PFD (A) was washed with water and the second one (B) was the control, i.e. unwashed PFD. Five freeze-dryings were performed per PFD product at a constant shelf temperature of 32° C., and the pressure was increased gradually from 0.3 to 1.2 mBar. The product appearance after freeze-drying under different pressures was assessed by visual comparison to a reference freeze-dried product which was unwashed concentrate (portion B) and freeze-dried at a pressure of 0.3 mBar. The results for product appearance after freeze-drying and water activity of freeze-dried products are shown in Table 2 and 3, respectively.

At the lowest pressure of 0.3 mBar, no difference in products appearance was observed for the two products (A and B), although unwashed FD product (B) had a higher $a_w$ of 0.08 (Table 2). For the unwashed product (B), increasing gradually the pressure from 0.5 to 1.2 mBar resulted in a gradual loss of pellet shape corresponding to a degree of appearance from 1 to 3 (Table 2). The bad product appearance at pressures in the range of 0.5-1.2 mBar was also confirmed by the high values of water activity ($a_w$) in the range of 0.21-0.35 (Table 3).

The product washed with water (A) was successfully freeze-dried at all tested pressures in the range of 0.3 to 1.2 mBar, and no visual change in product appearance (i.e. degree of 0) was seen (Table 2). The fact that product appearance and characteristics remained unchanged at all pressures tested was also confirmed by the very low value of the water activity ($a_w$) of 0.03, which was below the Limit of Detection (LOD) of 0.03 for the equipment (Table 3). This indicates that the product was very well dried (Table 3).

TABLE 2

Culture LGG: Comparison of product appearance of freeze-dried products of unwashed and washed cell concentrates with respect to a potential effect of the pressure (0.3 to 1.2 mBar) during freeze-drying. The washing ratio is 2, i.e. 2 volumes washing solution (water) per one volume concentrate.

| | Pressure during drying | | | | |
|---|---|---|---|---|---|
| | 0.3 mBar | 0.5 mBar | 0.7 mBar | 0.9 mBar | 1.2 mBar |
| Portion | Evaluation of product appearance after freeze-drying | | | | |
| A (washed with water) | 0 | 0 | 0 | 0 | 0 |
| B (No wash) | 0 | 0 | 1 | 2 | 3 |

Washing solutions: (A) water; (B) No washing.

TABLE 3

Culture LGG: Comparison of water activity of freeze-dried products of unwashed and washed cell concentrates with respect to a potential effect of the pressure (0.3 to 1.2 mBar) during freeze-drying. The washing ratio is 2, i.e. 2 volumes washing solution (water) per one volume concentrate.

| | Pressure during drying | | | | |
|---|---|---|---|---|---|
| | 0.3 mBar | 0.5 mBar | 0.7 mBar | 0.9 mBar | 1.2 mBar |
| Portion | water activity ($a_w$) of freeze-dried products | | | | |
| A (washed with water) | <0.03 | <0.03 | <0.03 | <0.03 | <0.03 |
| B (No wash) | 0.08 | 0.213 | 0.32 | 0.31 | 0.35 |

Washing solutions: (A) water; (B) No washing.

In conclusion, these results show that:

Washing of the cell concentrates reduces the risks of changes in product appearance during freeze-drying, especially at high pressure.

Washing of the cell concentrates with water allows drying at higher pressure of 1.2 mBar compared to the unwashed freeze-dried products with no change in visual product appearance. This was also confirmed by the very low value of water activity ($a_w$) of 0.03, which is below the Limit of Detection (LOD) for the equipment.

Even at a higher pressure of 1.2 mBar, washed freeze-dried product had the same low water activity ($a_w$) of less than 0.03 compared to a pressure of 0.3 mBar, which is below the Limit of Detection (LOD) of 0.03 for the equipment The findings in this example are in agreement with the results given in Examples 1, 2, 3, 4, 6, 7, 8 and 9; i.e. the washing of cell concentrates improves the drying efficiency by resulting in lower water activity compared to the unwashed freeze-dried products, even at higher pressure.

Example 11

Hardness of Washed Freeze-Dried Products

The experiment presented in this example was identical to that described in Example 2.

Five washed freeze-dried products were prepared (A-E) using a different washing ratio in the range of 0.5 to 10 (liters of water per liter of concentrate) as described in Example 2. Product (F) was the control, i.e. the unwashed freeze-dried product.

The aim of this example was to evaluate the effect of washing on the hardness of the freeze-dried pellets (Table 4). The hardness of the freeze-dried pellets was evident visually and by feeling after pressing the pellets physically by hand (Table 4). Washing the cell concentrate reduced the concentration of unused media components and fermentation products which resulted in less hard freeze-dried pellets (A-E), which can be easily broken compared to the unwashed (F) product. The washed products (A-E) also look and feel fluffier and most likely have a more porous. With regard to how hard it is to break the freeze-dried products, the pellet hardness of washed products (A-E) decreased from washing ratio 0.5 to 2 and a washing ratio of 2 resulted in similarly brittle freeze-dried pellets as washing ratios of 3 and 10. Based on these results it is expected that the washed freeze-dried product can be grinded more easily. Thus, less heat will be developed during grinding, the grinding step will be shortened and, consequently, better survival during grinding will be observed.

TABLE 4

Culture LGG: Evaluation of the effect of washing on freeze-dried pellet hardness with respect to how hard it is to break the freeze-dried products. Washing ratio from 0.5 to 10 volumes water per one volume concentrate.

| Portion | Ratio of washing solution (Liters of water per liter of concentrate) | Appearance |
|---|---|---|
| A | 0.5 | Very crisp pellets, yellow, rough surface, small pellets |
| B | 1 | Crisp pellets, light yellow, rough surface, easy to grind |
| C | 2 | Brittle pellets, light yellow, rough surface, easy to grind |
| D | 3 | Brittle pellets, light yellow, rough surface, easy to grind |
| E | 10 | Brittle pellets, white, rough surface, easy to grind |
| F(control) | Unwashed concentrate (No added water) | Very hard, sticky pellets, dark yellow, rough surface, small pellets |

(A) washing ratio 0.5; (B) washing ratio 1; (C) washing ratio 2; (D) washing ratio 3; (E) washing ratio 10; (F) No washing.

Overall the results from this study indicate that:
Washing the cell concentrate with water decreases the pellet hardness resulting in pellets that can be broken easily compared to the unwashed freeze-dried product.
With regard to how hard is to break the freeze-dried products, the pellet hardness of washed products decreased with increasing washing ratio from 0.5 to 2
With regard to how hard it is to break the freeze-dried products, the washing ratio of 2 resulted in similarly brittle freeze-dried pellets as the washing ratios 3 and 10.

Example 12

Wash of a *Lactobacillus acidophilus*, La-5

The strain La-5® is cultivated in 7000 liters MRS medium under standard conditions with controlled pH and temperature.
The culture is harvested at early stationary phase and concentrated 14-fold by centrifugation, using a continuous centrifuge Alfa-Laval MRPX 418 SGV-34C.
The concentrated culture (500 liters) is pumped into a tank, and 1000 liters of deionized water are added. The resulting suspension is agitated and concentrated to 500 liters using a continuous centrifuge Alfa-Laval MRPX 418 SGV-34C. The production process flow is shown in FIG. 15.
The addition of cryoprotective solution is performed as described in Example 1. The concentrated culture is freeze-dried.

Example 13

Wash of a *Bifidobacterium* Culture, BB-12®

The strain BB-12® is cultivated in 7000 liters MRS medium under standard conditions with controlled pH and temperature. The culture is harvested at early stationary phase and concentrated 14 fold by centrifugation, using a continuous centrifuge (Alfa-Laval MRPX 418 SGV-34C).
The concentrated culture (500 liters) is pumped into a tank, and 1000 liters of deionized water are added. The resulting suspension is agitated and concentrated to 50 liters using a continuous centrifuge. The production process flow is shown in FIG. 15.
The addition of cryo-protective solution is performed as described in Example 1. The concentrated culture is freeze-dried.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Example 14

*Lactococcus Lactis*, R-607-1: Comparison of Product Quality when Freeze-Dried Under Mild and Aggressive Conditions. Effect of High Pressure (0.5-0.95 mBar)

*Lactococcus lactis*, R-607-1® with deposit accession number DSM21404 was cultivated in 700 liters MRS. The bacteria in the fermentation broth were concentrated by centrifugation using a centrifuge CSA-6 Westfalia. After centrifugation, the bacterial concentrate was mixed with cryoprotective solution (300 g to 1000 g cell concentrate). Afterwards the bacterial suspension was frozen with liquid nitrogen in the form of pellets (i.e. PFD). The cryoprotective solution consisted of skim milk (14%), monosodium glutamate (6%) and water (80%). The frozen pellets of the bacterial suspension are called pre-freeze-dried product (i.e. PFD). Pre-freeze-dried product (PFD) in the form of frozen pellets (i.e. PFD) with a size of 1 to 5 mm in diameter was used for the freeze-drying trials carried out in the pilot scale described below. The PFD was kept at −50° C. until being freeze-dried.
The freeze-drying was performed in a Hetosicc freeze dryer, CD-10-1, Heto Lab equipment, Heto-Holten A/S, Allerod, Denmark.
The freeze-dryer can operate at pressures in the range of 0.2-1.5 mBar and is equipped with a heating plate temperature that operates in the range of −40 to +80° C. The condenser operates with an average temperature of −60° C. The amount of material required is between 0 and 10 kg. The freeze-dryer has 6 heating plates designed for Radiant drying and a supporting rack for the trays. The supporting rack for the trays is suspended in a weighing cell (see Atlas Pilot Freeze-drying Plant-RAY™, NIRO, DK). The weighing device is connected to a computer which allows the recording of the mass, i.e. the change in weight during drying due to removal of water, thereby assuring an accurate process control. The drying trays are located between the heating plates by hanging on the rack. Therefore, a maximum of 5 levels of trays can be positioned as the number of heating plates is 6. In this study, 2 trays made of anodised aluminium 470×250×35 mm, were positioned per level, so that in total 10 trays were present in the freeze-drying cabinet (2 trays per level×5 levels=10 trays).

Frozen pellets (PFD) of R-607-1 with a mass of 10 kg were put on the drying trays and afterwards placed in the freeze-drying chamber and dried with 4 different freeze-drying (FD) cycles as indicated below. Freeze-drying (FD) cycle A was a control cycle, i.e. a so-called mild cycle, with a constant heating plate temperature and a constant chamber pressure during the drying of 5° C. and 0.3 mBar, respectively. The other freeze-drying cycles (B, C and D) were carried out using more aggressive drying conditions. A higher pressure of 0.5, 0.7 and 0.95 mBar was applied for FD cycle B, C and D, respectively. The heating plate temperature was also increased from 5 to 50° C. Both pressure and heating plate temperature were kept constant during the drying process (B, C and D).

The end of the drying was reached when the change in weight during drying was below 0.1% per 1 hour, and the product temperature was not higher than 35° C.

The following freeze-drying cycles were used:

| Freeze-drying cycle | Pressure mBar | Heating plate temperature ° C. |
|---|---|---|
| A (Control) | 0.3 | 5° C. |
| B | 0.5 | 50° C. |
| C | 0.7 | 50° C. |
| D | 0.95 | 50° C. |

The water activity ($a_w$) of freeze-dried products was measured immediately after freeze-drying. Water activity ($a_w$) measurement was performed as described in Example 1.

The acidification activity in the freeze-dried culture was measured according to the International standard ISO 26323:2009 (IDF 213: 2009): "Milk products—Determination of the acidification activity of dairy cultures by continuous pH measurement (CpH)".

Acidification activity is qualified by the following parameters:
  $t_a$: The time it takes to start acidifying the standardized milk, i.e. the time in which the pH drops 0.08 pH units from the initial pH. The time $t_a$ is measured in minutes from the time of inoculation, t=0.
  pH-6h: The pH that is reached after 6 hours at 30° C. for this particular starter culture.
  The higher $t_a$ and pH-6h are, the longer the latency phase and, thus, the lower the acidification activity (Fernanda et al. 2004).

The evaluation of the appearance of the freeze-dried product after freeze-drying and the categorization was performed according to the grading described in Example 10.

Results

The aim of the present study was to investigate the effect of aggressive freeze-drying conditions (high pressure) on the quality of freeze-dried products of R-607-1. Examination was done by comparison of both water activity ($a_w$) and acidification activity ($t_a$, pH-6h) of freeze-dried products obtained by aggressive (B-D) and mild (A) FD cycles (see table above). The mild drying (A, reference drying) was carried out with a constant heating plate temperature of 5° C. and with a constant chamber pressure of 0.3 mBar. For the aggressive dryings (B-D), the pressure was increased from 0.3 mBar (A) to 0.5, 0.7 and 0.95 mBar, respectively for the cycles B, C and D. The heating plate temperature was also increased from 5 to 50° C., but it was kept the same for the three cycles B, C and D. Both pressure and heating plate temperature were kept constant during the drying process (A, B, C and D).

No significant difference was observed in acidification activity of FD products when dried with the mild (A) and aggressive freeze-drying conditions (B-D). The time $t_a$ was 91 min for the product obtained with the mild FD cycle compared to a $t_a$ of 93-97 min for the FD products generated with the more aggressive cycles (B-D). Aggressive FD cycles (B-D) also resulted in a product with a pH-6h value in the same range (4.9-5) to that of the mild FD cycle (pH-6h of 4.9).

Moreover, taking the precision of the analysis into consideration (Iso 26323:2009), the acidification activity of the FD products was not significantly different when the FD product was obtained by the mild cycles or by the aggressive FD cycles. Thus, it can be concluded that aggressive drying at pressured in the range of 0.5-0.95 mBar exerts no detrimental effect on the acidification activity of R-607-1.

Evaluation of freeze-dried products normally also includes the observation of the product appearance after freeze-drying because one of the desired characteristic is to avoid changes in the freeze-dried product appearance. The product appearance after freeze-drying with aggressive drying cycles (B-D) was assessed by visual comparison to a reference freeze-dried product which was obtained by drying with the mild FD cycle (A). No difference in products appearance was observed (Table 5). The fact that the FD product appearance and characteristics were not changed by the aggressive drying procedures (B-D) was also confirmed by a low value of water activity ($a_w$=0.03-0.05) of these FD products. This value was comparable to that of the FD product obtained by the mild drying cycle (A) (0.03) (Table 5).

Despite the fact that no significant differences between acidification activity and $a_w$ of FD products dried under aggressive or mild FD conditions were observed, a significant difference in the drying time was seen (FIG. 16). More aggressive drying cycles (B-D) resulted in approximately 3 times shorter drying times of between 11 and 14.5 h compared to 36 h for the mild FD cycle (A). Thus, the more aggressive cycles result in a much more efficient drying process, especially with regard to the energy costs and the productivity.

The main conclusions from the results presented in Example 14, which was performed with the culture R-607-1, are:

Product quality and performance of the products dried under aggressive conditions (0.5-0.95 mBar and 50° C.) were indistinguishable from those of product dried under 'mild' conditions (0.3 mBar and 5° C.).

No significant difference was observed in acidification activity ($t_a$ and pH-6h) of FD products when dried with the mild and aggressive freeze-drying conditions.

All freeze-dried products from the aggressive dryings were well dried and reached significantly lower water activity of less than 0.05 as compared to 0.03 for that of the mild drying.

No difference in product appearance was seen when comparing FD products obtained by the aggressive drying processes as compared to that obtained by a mild drying process.

Aggressive drying processes resulted in an approximately 3 times shorter drying time compared with that of the mild drying. This results in a much more efficient drying process, especially regarding the energy costs and productivity.

TABLE 5

CultureR-607-1: Comparison of product quality when freeze-dried under mild (A) and aggressive conditions (B-D) with respect to acidification activity ($t_a$, ph-6h), water activity ($a_w$) and product appearance.

| FD Cycle | FD Pressure (mBar) | pH-6h | $t_a$ | $a_w$ | Product appearance after freeze-drying |
|---|---|---|---|---|---|
| A | 0.3 | 4.9 | 91 | 0.03 | 0 |
| B | 0.5 | 4.9 | 93 | 0.03 | 0 |
| C | 0.7 | 5.0 | 94 | 0.05 | 0 |
| D | 0.95 | 5.0 | 97 | 0.05 | 0 |

A (5° C., 0.3 mBar);
B (50° C., 0.5 mBar);
C (50° C., 0.70 mBar);
D (50° C., 0.95 mBar)

Example 15

*Lactobacillus rhamnosus* LGG: Comparison of Product Quality when Freeze-Dried Under Mild and Aggressive Conditions. Effect of High Temperature (50-75° C.)

*Lactobacillus rhamnosus* (ATCC53103) was cultivated in 700 liters MRS. The bacteria in the fermentation broth were concentrated by centrifugation using a centrifuge CSA-6 Westfalia. After centrifugation, the bacterial concentrate was mixed with cryoprotective solution (300 g to 1000 g cell concentrate). Afterwards, bacterial suspension was frozen with liquid nitrogen in the form of pellets (i.e. PFD). The cryoprotective solution consisted of skim milk (14%), monosodium glutamate (6%) and water (80%). The frozen pellets of the bacterial suspension are called pre-freeze-dried product (i.e. PFD). Pre-freeze dried product (PFD) in the form of frozen pellets (i.e. PFD) with sizes of 1 to 5 mm in diameter were used. The PFD was kept at −50° C. until being freeze-dried. The freeze-drying was carried out as described in Example 14 with four different freeze-drying (FD) cycles as described below. Freeze-drying (FD) cycle A was a control cycle, i.e. a so-called mild cycle with a constant heating plate temperature and constant chamber pressure during the drying process of 5° C. and 0.3 mBar, respectively. For the aggressive dryings (B-D), the pressure was increased from 0.3 mBar (A) to 0.5 mBar and kept constant during the drying. The heating plate temperature was also increased from 5° C. to a constant temperature of 50° C. and 75° C., respectively, for drying cycles B and D. For cycle C the plate temperature was decreased from 75 to 50° C. after 45% water removal.

| Freeze-drying cycle | Pressure mBar | Heating plate temperature ° C. | Comments |
|---|---|---|---|
| A (Control) | 0.3 | 5° C. | |
| B | 0.5 | 50° C. | |
| C | 0.5 | 75° C. | Heating plate temperature is lowered to +50° C. after 45% water is removed |
| D | 0.5 | 75° C. | |

The water activity ($a_w$) of freeze-dried products was measured immediately after freeze-drying. Water activity ($a_w$) measurement was performed as described in Example 1.

The number of viable cells after freeze-drying and after storage test was determined as colony forming units (CFU) as described by Palmfeldt and Hahn-Hägerdal (2000), Int J Food Microbiol, 55(1-3):235-8. The evaluation of the appearance of the freeze-dried product after freeze-drying and the categorization was performed according to the grading described in Example 10.

Results

The aim of the present study was to investigate the effect of aggressive freeze-drying conditions (high heating plate temperature) on the survival of freeze-dried *Lactobacillus rhamnosus* LGG. Examination was done by comparison of viable cells (CFU) after freeze-drying of products that were freeze-dried with the mild cycle (A; 5° C. and 0.3 mBar) with products that were freeze-dried with the aggressive FD cycles (B-D; 50-75° C. and 0.5 mbar). The results are summarized in Table 6.

No significant difference was seen in viable cell count after freeze-drying (CFU) when increasing the heating plate temperature from 5° C. (A) to 50° C. (B) and 75° C. (C and D). Moreover, no visual structural change occurred for FD product when the heating plate temperature was increased from 5° C. to 75° C.

In addition, the stability of the product, i.e. the cell survival, was also studied during storage for 3 weeks in open bags at 30° C. and 30% RH (Table 6). Surprisingly, the mild FD conditions (A; heating plate temperature of 5° C. and pressure of 0.3 mBar) affect the cell survival negatively during storage. This FD (A) cycle resulted in the highest cell loss, and therefore, in the lowest viable cell count of 10.8 (log CFU/g) compared to that of 11.5 (log CFU/g) for drying cycle B, and 11-11.1 (log CFU/g) for drying cycles C and D, respectively. The results were also confirmed by flow cytometry (data not shown). Thus, it can be concluded that aggressive drying cycles (B-D) with a heating plate temperature of 50 and 75° C. or results in FD product with higher cell viability during storage compared to the mild FD conditions (A) with a heating plate temperature of 5° C.

Also, no visual change in the pellet structure was seen when the product was freeze-dried under high temperatures of 50 and 75° C. (B-D) as compared with a low temperature of 5° C. (A) (Table 6). The fact that there was no change in the pellet structure of the FD products that underwent aggressive drying cycles (B-D) was also confirmed by the rather low water activity of the FD product of less than 0.03, which was also below the Limit of Detection (LOD) of 0.03 for the equipment.

In addition, the more aggressive drying cycles (B-D) resulted in 3 times shorter drying times of 10-14.5 h compared with that of 36 h for the mild FD cycle (A) (FIG. 17). Thus, these were much more efficient drying processes, especially with regard to the energy cost and productivity.

The main conclusions from the results presented in Example 15 that were performed with the culture LGG are the following:

- Aggressive drying cycles (50 and/or 75° C. and 0.5 mBar) resulted in FD products with a higher cell viability after storage compared with the mild FD conditions (5° C. and 0.3 mBar), although the products showed a comparable viable cell count after freeze-drying (CFU).
- No difference in products appearance was seen when comparing FD products obtained by aggressive drying cycles (50; 75° C. and 0.5 mBar) compared with that of the mild drying cycle (5° C. and 0.3 mBar). This is in agreement with the conclusions drawn in Example 14 above.
- Freeze-dried products from the aggressive drying cycles were well dried. They reached the same water activity of less than 0.03 as those products of the mild drying. This was also below the Limit of Detection (LOD) of 0.03 for the equipment. This is in agreement with the conclusions drawn in Example 14.
- Aggressive drying cycles resulted in approximately 3 times shorter drying time as compared with that of the mild drying cycle, which results in much more efficient drying processes, especially regarding the energy costs and the productivity. This is in agreement with the conclusions drawn in Example 14.

TABLE 6

Culture LGG: Comparison of the product quality of products that were freeze-dried under mild (A) or aggressive conditions (B-D) with regard to the water activity ($a_w$), product appearance and cell survival (CFU) after freeze-drying and 3 weeks storage at 30° C. and 30% RH.

| FD Profile | Temperature-Heating plates (° C.) | Water activity aw | Start: after FD Log CFU/g | After 3 weeks storage Log CFU/g | Cell loss after storage Log loss CFU/g | Product appearance after freeze-drying |
|---|---|---|---|---|---|---|
| A (Control) | 5 | 0.03 | 11.6 | 10.8 | 0.8 | 0 |
| B | 50 | 0.03 | 11.5 | 11.5 | 0.0 | 0 |
| C | 75 → 50 | 0.03 | 11.5 | 11.1 | 0.4 | 0 |
| D | 75 | 0.03 | 11.3 | 11.0 | 0.3 | 0 |

A (5° C., 0.3 mBar);
B (50° C., 0.5 mBar);
C (75° C.→50° C., 0.5 mBar);
D (75° C., 0.5 mBar)

Example 16

*Streptococcus thermophilus*, ST-10255: Production Scale Freeze-Drying at Aggressive Drying Conditions. Comparison of Product Quality with a Reference Product from a Pilot Scale that was Obtained by Mild Freeze-Drying Conditions Frozen pellets of *Streptococcus thermophilus* strain ST10255 in skim milk and monosodium glutamate with a size of 1 to 5 mm in diameter were used for the freeze-drying trials carried out at pilot scale as described below. The frozen pellets were kept at −50° C. until being freeze-dried. Two dryings were carried out. One was done at production scale under aggressive drying condition, and the second one was done at pilot scale under mild freeze-drying conditions (the reference).

Production Scale Freeze-Drying

The freeze-drying was carried out at a production scale with the Atlas Ray™ Batch Dryer concept with continuous De-Icing System (Atlas Ray™; GEA Niro) as shown in the Table. The tray area was 140 m², which translates to a batch size of up to 2000 kg. The heating plates provide heat radiation to the trays. The maximum sublimation rate was 330 kg water/hour.

The frozen pellets of ST-10255 were freeze-dried in 2 steps.

Primary drying of the material was performed at a pressure of 0.6 mBar and a heating plate temperature of 65° C. This step was performed for a period of time that lasted at least 10 h; or until at least 75% water is removed, and the temperature of the material does not exceed 35° C. (i.e. the product temperature).

The secondary drying was performed at a temperature of 35° C. and the same pressure of 0.6 mBar. The temperature of the material did not exceed 35° C. This step was performed for a period of 11 hours.

Pilot Scale Trial Freeze-Drying

As a reference, a drying cycle was performed at Pilot scale using the same PFD product as used for the production scale trial. Freeze-drying was carried out as described in Example 14 with a freeze-drying cycle involving a constant heating plate temperature of 5° C. and a constant chamber pressure of 0.3 mBar.

The following freeze-drying cycles were used:

| Scale | Load in FD cabinet (kg) | FD Profiles | | Comment |
|---|---|---|---|---|
| | | Pressure (mBar) | Heating plate temperature (° C.) | |
| Pilot | 10 | A mild | 0.3 | 5 | |
| Production | 2000 | B aggressive | 0.6 | 65 | Secondary drying was done at 35° C. |

The water activity ($a_w$) of the freeze-dried products was measured immediately after freeze-drying. Water activity ($a_w$) measurement was performed as described in Example 1. The determination of the acidification activity ($t_a$ and pH-6h) was performed as described in Example 14. The evaluation of the appearance of the freeze-dried product after freeze-drying and the categorization was performed according the grading described in Example 10.

Results

Two drying processes were carried out. One drying process was performed in a Pilot scale freeze-dryer using a mild freeze-drying cycle (A) operating at temperature of 5° C. and a pressure of 0.3 mBar. The second drying process was performed in a production scale freeze-dryer with aggressive conditions, i.e. with a heating plate temperature of 65° C. and a pressure of 0.6 mBar in the primary drying. Results from both dryings are summarized in Table 7.

Taking the precisions of the analysis into consideration (ISO 26323:2009), no significant difference was observed in acidification activity of the product that was dried under mild (A) conditions at the Pilot scale compared with that dried under aggressive freeze-drying conditions (B) at production scale.

$t_a$: Time ($t_a$) was 47 min for the product obtained with the mild FD cycle (A) compared to a $t_a$ of 53 min for the aggressive FD product (B) that was produced at production scale.

pH6h: The FD product from the aggressive cycle from the production scale process had the same pH-6h as compared to the product obtained by the mild FD cycle at pilot scale.

With respect to water activity and product appearance after freeze-drying:

No visual change in pellets structure was seen when the product was freeze-dried at production scale with an aggressive cycle (B) compared to the product dried at Pilot scale under mild drying conditions (A) (Table 7).

A comparable water activity was obtained. The water activity of the FD product that was produced with aggressive drying was 0.08 compared to that of 0.03 for the FD product that was obtained by the mild drying cycle (A) at Pilot scale.

Overall, the conclusions from the results presented in Example 16 carried out at production scale with culture ST-10255 are in agreement with the conclusions drawn in Examples 14 (culture R-607-1) and 15 (culture LGG).

Product quality and performance of the products dried under aggressive conditions (0.65 mBar and 60° C.) at production scale were indistinguishable from product that was dried under mild conditions (0.3 mBar and 5° C.) at pilot scale.

No significant difference was observed in the acidification activity ($t_a$ and pH-6h) of the FD product when dried with the mild or aggressive freeze-drying conditions at Pilot and Production scale, respectively.

The freeze-dried product from the aggressive drying process from the production scale was well dried and reached a low water activity of 0.08 as compared to 0.03 for that of the mild drying at Pilot scale.

No difference in the product appearance was seen when comparing the FD products obtained by the aggressive drying from production scale compared to that of the mild drying from pilot scale.

TABLE 7

Culture ST-10255: Comparison of the product quality when freeze-dried under mild (A) and aggressive conditions (B-D) with respect to the acidification activity ($t_a$, ph-6h), water activity ($a_w$) and product appearance.

| | | | Freeze-dried product quality | | |
|---|---|---|---|---|---|
| Scale | FD profile | pH-6h | Ta | Water activity | Product appearance |
| Pilot | A (mild) | 5.1 | 47 | 0.03 | 0 |
| Production | B (aggressive) | 5.1 | 53 | 0.08 | 0 |

A (5° C., 0.3 mBar);
B (65° C. → 35° C., 0.6 mBar).

REFERENCES

Ferreira, V. et al. "Survival of *Lactobacillus sakei* during heating, drying and storage in the dried state when growth has occurred in the presence of sucrose or monosodium glutamate." *Biotechnology Letters* 27(4) (2005): 249-52.

de Valdez G F, et al. "Effect of Drying Medium on Residual Moisture Content and Viability of Freeze-Dried Lactic Acid Bacteria." *Appl Environ Microbiol.* 49(2) (1985): 413-15.

Kurtmann L, et al. "Water activity-temperature state diagrams of freeze-dried *Lactobacillus acidophilus* (La-5): Influence of physical state on bacterial survival during storage." *Biotechnol. Prog* 25(1) (2009): 265-70.

Laroche C, Fine F, and Gervais P. "Water activity affects heat resistance of microorganisms in food powders." *International Journal of Food Microbiology* 97.3 (2005): 307-15.

Patel S M, Doen T, Pikal M J. "Determination of End Point of Primary Drying in Freeze-Drying Process Control." *AAPS Pharm Sci Tech* 11.1 (2010): 73-84.

Stadhouders et al, "Preservation of starters and mass production of starter bacteria", Neth. Milk Dairy J. 23, 182-199. 1969.

Fernanda et al. (2004), Collapse temperature of bacterial suspensions: the effect of cell type and concentration. Cryoletters 25[6], 425-34.

Palmfeldt J and Hahn-Hägerdal B. "Influence of culture pH on survival of *Lactobacillus reuteri* subjected to freeze-drying." Int J Food Microbiol. 55.1-3 (2000): 235-38.

PATENT LITERATURE

WO2006/125446
U.S. Pat. No. 7,037,708B1,
WO99057242,
WO2012088261,
WO2012076665

Strain *Streptococcus thermophilus* ST6008 was deposited at Deutsche Sammlung on Mikroorganismen and Zellkulturen GmbH, Mascheroder Weg 1b, D-38124 Braunschweig, Germany, under accession number DSM 18111 on Mar. 23, 2006. Strain *Bifidobacterium animalis* BB-12® was deposited at Deutsche Sammlung von Mikroorganismen and Zellkulturen GmbH, Mascheroder Weg 1b, D-38124 Braunschweig, Germany, under accession number DSM15954 on Sep. 30, 2003. Strain *Bifidobacterium animalis* BB-12® free was deposited at Deutsche Sammlung von Mikroorganismen and Zellkulturen GmbH, Mascheroder Weg 1b. D-38124 Braunschweig, Germany, under accession number DSM17281 on Apr. 28, 2005.

The invention claimed is:

1. A process for reducing the water activity in a bacteria-containing concentrate comprising:
    (a) adding an aqueous solution to a first bacteria-containing concentrate to provide a bacteria-containing suspension, wherein the volume of the added aqueous solution is in the range of from 0.3 liters to 10 liters per liter of said first bacteria-containing concentrate;
    (b) concentrating said bacteria-containing suspension to provide a second bacteria-containing concentrate; and
    (c) freeze-drying said second bacteria-containing concentrate to obtain a freeze-dried second bacteria-containing concentrate,
    wherein the freeze-dried second bacteria-containing concentrate has a reduced water activity as compared to a freeze-dried bacteria-containing concentrate prepared under same drying conditions and drying time but without steps (a) and (b).

2. The process according to claim 1, wherein the volume of the aqueous solution is in the range of from 0.5 liter to 6 liters per liter of said first bacteria-containing concentrate.

3. The process according to claim 1, wherein the concentrating in step (b) comprises a centrifuging step.

4. The process according to claim 1, wherein the concentrating in step (b) comprises a filtering step, wherein said filtering step comprises microfiltration or ultrafiltration.

5. The process according to claim 4, wherein said filtering step comprises tangential filtration.

6. The process of claim 1, further comprising prior to step (a) obtaining the first bacteria-containing concentrate by centrifuging a fermentation broth.

7. The process of claim 6, wherein the first bacteria-containing concentrate is concentrated 5 to 25 times relative to the volume of the fermentation broth.

8. The process of claim 1, wherein said bacteria-containing concentrate is a lactic acid bacteria-containing concentrate.

9. The process of claim 1, wherein said bacteria-containing concentrate comprises a bacteria selected from the group consisting of *Acetobacter, Bifidobacterium, Carnobacterium, Enterococcus, Lactococcus, Lactobacillus, Leuconostoc, Pediococcus, Oenococcus, Propionibacterium*, and *Streptococcus*.

10. The process of claim 9, wherein said bacteria-containing concentrate comprises at least one lactic acid bacteria of a species selected from the group consisting of *Leuconostoc* spp., *Bifidobacterium* ssp., *Lactococcus lactis, Lactococcus cremoris, Lactobacillus acidophilus, Lactobacillus casei, Lactobacillus kefir, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sake, Lactobacillus reuteri, Lactobacillus lactis, Lactobacillus delbreuckii, Lactobacillus plantarum*, and *Streptococcus thermophilus*.

11. The process of claim 1, wherein the bacteria are of a strain selected from the group consisting of the strains deposited with the German Collection of Microorganisms and Cell Cultures (DSMZ) under the accession numbers DSM15954, DSM17281, DSM13241, and DSM18111, the strain that was deposited with the American Tissue Type Collection Center under the accession number ATCC53103, and a mutant of any of these.

12. The process of claim 1, wherein the aqueous solution is water.

13. The process of claim 1, wherein said aqueous solution comprises from 1 to 300 g/l of a carbohydrate.

14. The process of claim 13, wherein said carbohydrate is sucrose and/or trehalose.

15. The process of claim 1, further comprising prior to step (b) mixing the aqueous solution and the first bacteria-containing concentrate.

16. The process of claim 1, further comprising repeating the adding and concentrating steps.

17. The process of claim 1, further comprising adding a cryo-protectant and/or stabilizer to the second bacteria-containing concentrate.

18. The process of claim 1, wherein the volume of the aqueous solution is in the range of from 1.0 to 2.0 liters per liter of the first bacteria-containing concentrate.

19. The process of claim 1, wherein step (c) comprises freeze-drying said second bacteria-containing concentrate at a pressure of 0.5 to 2.0 mBar, and a applying a heating plate temperature of from 50° C. to 85° C.

20. The method of claim 1, wherein the aqueous solution is an aqueous buffer.

21. The method of claim 1, wherein the aqueous solution comprises carbohydrates, polysaccharides, saccharides, and combinations thereof.

* * * * *